United States Patent [19]

Van Lommen et al.

[11] Patent Number: 4,813,998
[45] Date of Patent: Mar. 21, 1989

[54] HERBICIDAL 1H-IMIDAZOLE-5-CARBOXYLIC ACID DERIVATIVES

[75] Inventors: Guy R. E. Van Lommen, Berlaar, Belgium; William R. Lutz, Riehen, Switzerland; Jozef F. E. Van Gestel, Vosselaar, Belgium

[73] Assignee: Janssen Pharmaceutica N.V., Beerse, Belgium

[21] Appl. No.: 88,445

[22] Filed: Aug. 24, 1987

Related U.S. Application Data

[63] Continuation-in-part of Ser. No. 944,284, Dec. 19, 1986, abandoned, which is a continuation-in-part of Ser. No. 833,623, Feb. 27, 1986, abandoned.

[51] Int. Cl.$^4$ ............... A01N 43/50; C07D 405/04
[52] U.S. Cl. .............................. 71/92; 71/90; 540/543; 540/587; 540/593; 546/15; 546/16; 546/18; 546/106; 546/159; 546/162; 548/318; 548/336
[58] Field of Search ............ 548/318, 336; 71/90, 71/92; 546/15, 16, 18, 159, 106; 540/543, 587, 593

[56] References Cited

U.S. PATENT DOCUMENTS

| | | | |
|---|---|---|---|
| 3,485,917 | 12/1969 | Godefroi et al. | 548/343 |
| 3,873,297 | 3/1975 | Kupelian | 71/78 |
| 4,182,624 | 1/1986 | Soder et al. | 548/336 |
| 4,191,764 | 3/1980 | Beard | 514/397 |
| 4,339,448 | 7/1982 | Dockner et al. | 514/397 |
| 4,369,186 | 1/1983 | Beck et al. | 514/397 |
| 4,639,447 | 1/1987 | Roeser et al. | 514/397 |

OTHER PUBLICATIONS

Godefroi et al., J. Med. Chem., 10 (6), pp. 1160–1161 (1967).
Vanbreuseghem et al., Chemotherapia, 12 (2), pp. 107–122 (1967).
Thornber, Chem. Soc. Rev., 8 (4), pp. 563–580 (1979).

*Primary Examiner*—Richard A. Schwartz

[57] ABSTRACT

Novel herbicidal 1-heterocyclyl-1H-imidazole-5-carboxylic acid derivatives, compositions containing these compounds as active ingredients, and a method for controlling weeds, preferably selectively in crops of useful plants. Further the invention also relates to a process for making these novel compounds.

22 Claims, No Drawings

HERBICIDAL 1H-IMIDAZOLE-5-CARBOXYLIC ACID DERIVATIVES

This is a continuation-in-part of application Ser. No. 944,284 filed Dec. 19, 1986 now abandoned, which in turn is a continuation-in-part of application Ser. No. 833,623 filed Feb. 27, 1986, now abandoned.

BACKGROUND OF THE INVENTION

In U.S. Pat. No. 3,485,917 there are described a number of 1H-imidazole-5-carboxylic acids as antifungals.

The present invention relates to novel herbicidal 1-heterocyclyl-1H-imidazole-5-carboxylic acid derivatives, compositions containing these compounds as active ingredients, and a method for controlling weeds, preferably selectively in crops of useful plants. Further the invention also relates to a process for making these novel compounds.

DESCRIPTION OF THE INVENTION

The present invention is concerned with herbicidally active 1-heterocyclyl-1H-imidazole-5-carboxylic acid derivatives having the formula

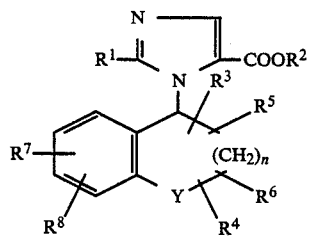

a stereochemically isomeric form thereof, or a salt thereof, or a quaternised form thereof, or a N-oxide thereof, wherein $R^1$ is hydrogen or mercapto, $R^2$ is hydrogen, $C_1$-$C_7$alkyl, $C_3$-$C_7$alkenyl, $C_3$-$C_7$alkynyl, $C_3$-$C_7$cycloalkyl, $C_1$-$C_7$alkyloxy-$C_1$-$C_7$alkyl, or aryl$C_1$-$C_5$alkyl;

n is zero, one or two;

Y is a group $—CH_2—S(O)_m—$, $—CH_2—O—$, $—CH_2—N(E)—$, or $—CH=N—$, wherein the hereoatom is linked to the carbon atom of the benzene ring and wherein m is zero, one or two;

E is hydrogen, $C_1$-$C_5$alkyl, $C_1$-$C_5$alkanoyl, or 4-methylphenylsulfonyl;

$R^3$, $R^4$, $R^5$ and $R^6$ are each independently hydrogen, $C_1$-$C_6$alkyl, mono- and di-(aryl)$C_1$-$C_5$alkyl, $C_1$-$C_6$alkyloxy, halo, $C_3$-$C_7$alkenyl, $C_1$-$C_5$alkyl substituted with one to three halo atoms, $C_1$-$C_5$alkyloxy substituted with one to three halo atoms or aryl; or $R^3$ and $R^4$ together may form a used benzene residue which may optionally be substituted with one or two substituents each independently selected from hydrogen, $C_1$-$C_5$alkyl, $C_1$-$C_6$alkyloxy, halo, $C_1$-$C_5$alkyl substituted with one to three halo atoms, $C_1$-$C_5$)alkyloxy substituted with one to three halo atoms, nitro, amino and $—NH—CO—G$; or where $R^3$ and $R^4$ are geminally substituted, they may form a spirocyclic carbon ring with 3 to 7 carbon atoms; and $R^7$ and $R^8$ are each independently hydrogen, $C_1$-$C_5$alkyl, $C_1$-$C_5$alkyloxy, halo, $C_1$-$C_5$alkyl substituted with one to three halo atoms, $C_1$-$C_5$alkylxoy substituted with one to three halo atoms, cyano, nitro, amino, mono- or di-$C_1$-$C;Hd 5$alkylamino or $—NH—CO—G$;

G is $C_1$-$C_6$alkyl; and aryl is phenyl optionally substituted with one to three substituents each independently selected from $C_1$-$C_5$alkyl, $C_1$-$C_5$alkyloxy and halo;

whereby the radicals $R^3$, $R^4$, $R^5$ and $R^6$ as defined above may be substituted to any carbon atom making up the Y containing part of the bicyclic ring system, including the $CH_2$ or CH-groups of either the $—(CH_2)_n—$ or $—CH_2S—$, $—CH_2O—$, $—CH_2N(E)—$ or $—CH=N—$ fragments.

Surprisingly, the compounds of formula (I) exhibit strong herbicidal properties, and are therefore useful to control weeds. This property gains importance by the fact, that some crops of useful plants are not damaged, or are only slightly harmed at high dosages when treated with compounds of formula (I). Consequently, the compounds of formula (I) are valuable selective herbicides in crops of useful plants, such as sugar beet, rape, soybeans, cotton, sunflower, cereals, especially wheat, barley, rye and oats, rice, both upland rice and paddy rice, and maize. Especially in rice crops a broad range of application rates can be employed, preferably if the rice crops are transplated rice crops, and if the compounds of formula (I) are applied after transplantation. In maize crops selective herbicidal action is observed both at preemergence and at postemergence treatment.

The active ingredients (a.i.) of formula (I) are usually applied at application rates of 0.01 to 5. kg of active ingredient per hectare in order to achieve satisfying results. Sometimes, depending on the environmental conditions, the application rates may exceed the above designated limitations. However, the preferred application rates are between 0.05 kg and 1.0 kg a.i. per hectare.

As used in the foregoing definitions $C_1$-$C_5$alkyl denotes straight or branch chained saturated hydrocarbon radicals having from 1 to 5 carbon atoms, e.g. methyl, ethyl, n-propyl, isopropyl, the four butyl isomers and the pentyl isomers; $C_1$-$C_6$ and $C_1$-$C_7$alkyl include $C_1$-$C_5$alkyl radicals and the higher homologs thereof having respectively 6 or 7 carbon atoms; halo is fluoro, chloro, bromo or iodo, with fluoro and chloro being preferred; $C_3$-$C_7$alkenyl defines straight and branch chained hydrocarbon radicals containing one double bond and having from 3 to 7 carbon atoms such as, for example, allyl, 3-butenyl, 2-butenyl, 2-pentenyl, 3-pentenyl, methallyl, or 3-methyl-2-butenyl, with allyl and methallyl being preferred; $C_3$-$C_7$alkynyl defines straight and branch chained hydrocarbon radicals containing one triple bond and having from 3 to 7 carbon atoms such as, for example, propargyl, 2-butynyl, 3-butynyl, 2-pentynyl, 3-pentynyl or 4-pentynyl, with propargyl being preferred; $C_3$-$C_7$cycloalkyl is generic to cyclopropyl, cyclobutyl, cyclopentyl, cyclohexyl and cycloheptyl, with cyclopentyl and cyclohexyl being preferred; $C_1$-$C_5$alkyloxy denotes, for example, methoxy, ethoxy, n-propyloxy, isopropyloxy, the four butyloxy isomers or the pentyloxy isomers; $C_1$-$C_7$alkyloxy-$C_1$-$C_7$alkyl denotes for example methoxymethyl, methoxyethyl, methoxypropyl, ethoxymethyl, ethoxyethyl, ethoxypropyl, propoxymethyl, propoxyethyl, propoxypropyl, isopropoxymethyl, isopropoxyethyl, isopropoxypropyl, 2-methoxypropyl, 2-ethoxypropyl, 2-methyloxybutyl, 3-methoxybutyl, 2-ethoxybutyl, or 3-ethoxybutyl; and alkanoyl denotes formyl, acetyl, propionyl, butyryl, isobutyryl, valeryl, isovaleryl or pivaloyl.

As typical examples of mono- and di-(aryl)$C_1$–$C_5$alkyl there may be mentioned benzyl, phenylethyl, 4-chlorobenzyl, 4-chlorophenylethyl, 4-methoxybenzyl, 3-methoxybenzyl or benzhydryl with benzyl being preferred.

As typical examples of halo substituted $C_1$–$C_6$alkyl and halo substituted $C_1$–$C_6$alkyloxy there may be mentioned fluoromethyl, chloromethyl, trifluoromethyl or difluoromethoxy.

The condensed benzoheterocyclic system being attached to the imidazole ring encompasses the following typical structures, which may further be substituted with the substituents $R^3$, $R^4$, $R^5$, $R^6$, $R^7$ and $R^8$:

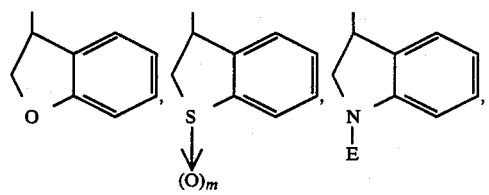

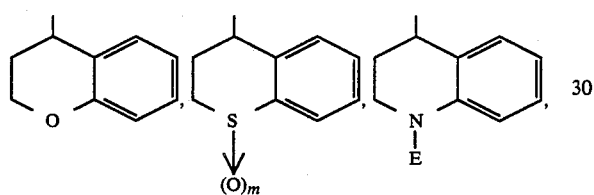

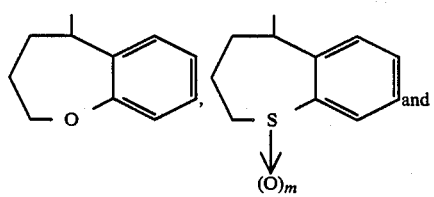

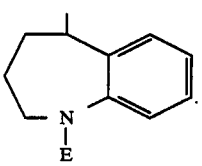

As defined hereinabove, $R^3$ and $R^4$ together with the two carbon atoms to which they are attached may form an optionally substituted benzene ring, in case these two carbon atoms are vicinally substituted. As such, the Y-containing heterocycle carries two condensed benzene rings, and typical examples thereof are represented by the following formulae:

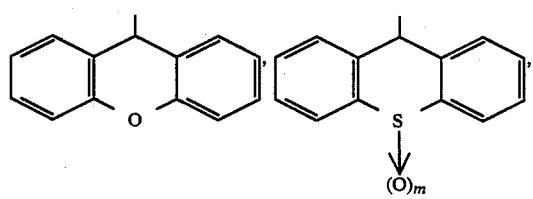

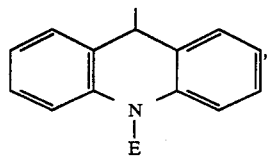

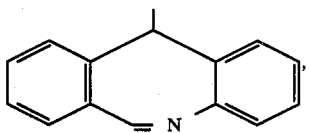

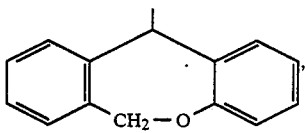

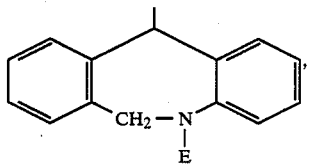

The above strucutres being optionally substituted with the various radicals $R^3$, $R^4$, $R^5$, $R^6$, $R^7$ and/or $R^8$.

As further defined hereinabove, wherein $R^3$ and $R^4$ are attached to the same carbon atom, they may also form a spirocyclic ring together with said carbon atom to which they are attached. Typical embodiments of such spirocyclic rings are cyclopropane, cyclobutane, cyclopentane, cyclohexane and cycloheptane.

Depending on the nature of the moiety linked to the imidazole in position 1 and/or the group $R^2$ the compounds of formula (I) contain asymmetrical carbon atoms. Unless otherwise mentioned or indicated, the chemical designation of compounds denotes the mixtures of all stereochemically isomeric forms. These mixtures contain all diastereomeres and enantiomeres of the basic molecular structure.

Pure isomeric forms of these compounds can be separated from the mixtures by conventional separation methods. Preferably, if a specific stereochemical form is desired, said compound will be synthesized by stereoselective methods of preparation. These methods will advantageously employ optically active starting materials.

The invention also comprises the use of the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

Examples of salt-forming mineral acids are hydrofluoric acid, hydrochloric acid, hydrobromic acid, hydroiodic acid, sulfuric acid, nitric acid, chloric acid, perchloric acid or phosphoric acid. Preferred salt-forming sulfonic acids are toluenesulfonic acid, benzenesulfonic acid, methanesulfonic acid or trifluoromethane sulfonic acid. Preferred salt-forming carboxylic acids are acetic acid, trifluoroacetic acid, benzoic acid, chloroacetic acid, phthalic acid, maleic acid, malonic acid and citric acid. Phosphorus containing acids are the various phosphonous acids, phosphonic acids and phosphinic acids.

Preferred salt-forming alkali metal hydroxides and earth alkaline metal hydroxides are the hydroxides of lithium, sodium, potassium, magnesium or calcium, most preferably those of sodium or potassium. Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine, diethanolamine and 1,4-diazabicyclo[2.2.2]octane being most preferred. Examples of quaternary ammonium bases are, in general, the cations of haloammonium salts, e.g. the tetramethylammonium cation, the trimethylbenzylammonium cation, the trieethylbenzylammonium cation, and also the ammonium cation.

As defined hereinabove, the invention also comprises the quaternised forms of the compounds of formula (I), said quaternised forms being represented by the formula

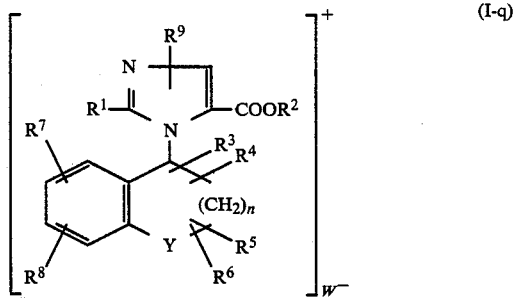

(I-q)

wherein $R^1$, $R^2$, $R^3$, $R^4$, $R^5$, $R^6$, $R^7$, $R^8$ and n are as defined hereinabove whereby $R^1$ preferably is hydrogen; $R^9$ is $C_1$–$C_5$alkyl optionally substituted with $C_1$–$C_5$alkyloxy, $C_1$–$C_5$alkylthio, $C_1$–$C_5$alkylcarbonyl, $C_1$–$C_5$alkyloxycarbonyl, $C_1$–$C_5$alkyl, phenyl or phenylcarbonyl; or $C_3$–$C_7$alkynyl or $C_3$–$C_7$alkenyl optionally substituted with phenyl; said phenyl as used in the definition of $R^9$ being optionally substituted with one to three halo, nitro, cyano, $C_1$–$C_5$alkyl, $C_1$–$C_5$alkyloxy or trifluoromethyl substituents.

Preferably $R^9$ is allyl, methallyl, propargyl or $C_1$–$C_4$alkyl optionally substistuted with $C_1$–$C_5$alkyl, phenyl or phenylcarbonyl; said phenyl being optionally substituted with one or two methyl, methoxy or halo radicals.

W is an organic or inorganic anion and preferably is hydroxy, alkyloxy or an anion arising from an acid such as hydrofluoric acid, hydrochloric acid, hydrobromic acid, hydroiodic acid, sulfuric acid, nitric acid, chloric acid, perchloric acid, phosphoric acid, dialkylphosphoric acid, 4-methylbenzenesulfonic acid, benzenesulfonic acid, methanesulfonic acid, trifluoromethylsulfonic acid, acetic acid, trifluoroacetic acid, benzoic acid, chloroacetic acid, phtalic acid, maleic acid, malonic acid, citric acid and more preferably is halo, 4-methylphenylsulfonate, methanesulfonate, 4-bromophenylsulfonate or dialkylphosphate.

Moreover, as defined hereinabove the invention also comprises the N-oxides which the compounds of formula (I) are able to form either in the imidazole moiety or in any N-containing radical possibly making up the structure of the compounds of formula (I), e.g., Y being —$CH_2$—N(E)— or —CH=N—. Preferably, the N-oxide is located in the imidazole moiety.

Preferred compounds within the present invention are those wherein $R^2$ is hydrogen or $C_1$–$C_7$alkyl; Y is —$CH_2$—O—, —$CH_2$—N(E)— or —$CH_2$S—; $R^3$, $R^4$, $R^5$ and $R^6$ are each independently hydrogen, $C_1$–$C_6$alkyl, aryl or (aryl)$C_1$–$C_5$alkyl, or where $R^3$ and $R^4$ are geminally substituted they may form a spirocyclic carbon ring with 3 to 7 carbon atoms; and $R^7$ and $R^8$ are each independently hydrogen, $C_1$–$C_5$alkyl, $C_1$–$C_5$alkyloxy, halo or cyano.

Particularly preferred compounds within the present invention are those preferred compounds wherein $R^2$ is hydrogen or $C_1$–$C_4$alkyl; n is zero or one; $R^3$ and $R^4$ are each independently hydrogen or $C_1$–$C_4$alkyl, or where $R^3$ and $R^4$ are geminally substituted they may form a spirocyclic carbon ring with 3 to 7 carbon atoms; $R^5$ and $R^6$ are both hydrogen; and $R^7$ and $R^8$ are each independently hydrogen, methyl, methoxy or halo.

More particularly preferred compounds are those particularly preferred compounds wherein $R^2$ is hydrogen or methyl; Y is —$CH_2$—O—; $R^3$ and $R^4$ are each independently hydrogen or $C_1$–$C_4$alkyl, or where $R^3$ and $R^4$ are geminally substituted they may form a cyclopentane or cyclohexane ring; and $R^7$ and $R^8$ are each independently hydrogen or halo.

The most preferred compounds of this invention are selected from the group consisting of methyl 1-(2,3-dihydro-4H-1-benzopyran-4yl)-1H-imidazole-5-carboxylate, methyl 1-(2,3-dihydro-2,2-dimethyl-4H-1-benzopyran-4-yl)-1H-imidazole-5-carboxylate, methyl 1-(6-bromo-2,3-dihydro-4H-1-benzopyran-4-yl)-1H-imidazole-5-carboxylate, methyl 1-[3,4-dihydrospiro[2H-1-benzopyran-2,1'-cyclohexan]-4-yl]-1H-imidazole-5-carboxylate, methyl 1-[3,4-dihydrospiro[2H-1-benzopyran-2,1'-cyclopentan]-4-yl]-1H-imidazole-5-carboxylate, methyl 1-[(3,4-dihydrospiro[2H-1-benzopyran-2,1'-cyclopentan]-4-yl]-2-mercapto-1H-imidazole-5-carboxylate, methyl (trans)-1-(2,3-dihydro-2-methyl-4H-1-benzopyran-4-yl)-1H-imidazole-5-carboxylate, methyl 1-(2,3-dihydro-2,3-dimethyl-4H-1-benzopyran-4-yl)-1H-imidazole-5-carboxylate, methyl 1-(2,3-dihydro-3,3-dimethyl-4H-1-benzopyran-4-yl)-1H-imidazole-5-carboxylate, the salts and possible stereoisomeric forms thereof.

The preparation of the compounds of formula (I) is generally carried out by the following methods.

The compounds of formula (I) can be obtained by condensing a compound of formula

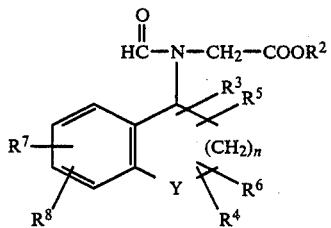

wherein $R^2$, $R^3$, $R^4$, $R^5$, $R^6$, $R^7$, $R^8$, n and Y are as defined hereinabove, with a $C_1$–$C_4$alkyl ester of formic acid in the presence of suitable base such as, for example, an alkali metal alkoxide or hydride, e.g., sodium methoxide, potassium ethoxide, sodium hydride, lithium hydride, and the like, in a reaction-inert solvent; and treating the resultant intermediate of formula

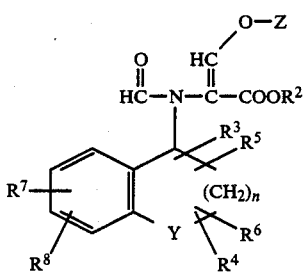

wherein $R^2$, $R^3$, $R^4$, $R^5$, $R^6$, $R^7$, $R^8$, n and Y are as defined hereinabove and Z is an alkali metal atom, (a) with an alkali isothiocyanate in the presence of an acid, thus obtaining a 2-mercaptoimidazole of formula

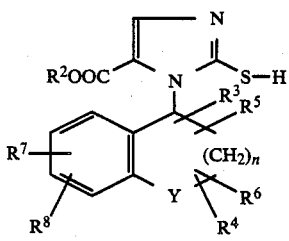

or the 2-thioximidazole tautomeric form thereof, wherein $R^2$, $R^3$, $R^4$, $R^5$, $R^6$, $R^7$, $R^8$, n and Y are as defined hereinabove, which optionally is converted into a compound of the formula

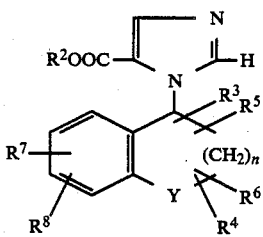

by reacting the starting compound (Ia) with sodium nitrite in the presence of nitric acid in an aqueous medium; or with Raney-nickel in the presence of a lower aliphatic alcohol, preferably ethanol, at a temperature between 40° C. and 80° C.; or also by treating the starting compounds (Ia) with an aqueous hydrogen peroxide solution preferably in the presence of a carboxylic acid, e.g. acetic acid; or by photochemical oxidation or also by treatment with alkali-hypochlorite; or (b) with a carboxylic acid amide of 1 to 3 carbon atoms, preferably formamide, in the presence of an acid at a temperature between 50° C. and 250° C., preferably between 120° C. and 170° C.; or (c) with an excess of ammonium carbonate or hydrogen carbonate in a suitable solvent, which may be a reaction-inert solvent or an acid, at a temperature between 20° C. and 200° C., preferably between 25° C. and the reflux temperature of the reaction mixture.

In the afore-mentioned process reaction-inert solvents are, for example, aromatic hydrocarbons such as benzene, methylbenzene or dimethylbenzene; ethers such as, for example, diethylether, tetrahydrofuran or dioxane; or other aprotic organic solvents. For the cyclization-reaction of the imidazole ring structure, strong mineral acids such as hydrohalic acids, e.g. hydrochloric acid, are most conveniently employed. In the ring-forming variant (c) also other acids, e.g. acetic acid, can be used. In this reaction an excess of acid of 5 to 50, preferably of 15 to 40 times the required molar amount is most preferably used. The excess of ammonium salt in this process is 2 to 50, preferably 10 to 30 times the required molar amount.

The quaternised forms of the compounds of formula (I) can conveniently be prepared by reacting a compound of formula (I) with a reagent of formula $$R^9-W^1 \qquad (IX),$$

wherein $R^9$ is as defined hereinabove and $W^1$ is an appropriate leaving group such as, for example, halo, e.g. chloro, bromo, iodo; an alkyl- or arylsulfonyloxy group, e.g. methylsulfonyloxy, 4-methylphenylsulfonyloxy or 4-bromophenylsulfonyloxy; or a dialkylphosphate group; thus preparing those quaternary compounds of formula (I-q) as defined hereinabove, wherein W is $W^1$. The reaction of (I) with (VII) is preferably conducted in a suitable solvent such as, for example, a hydrocarbon, e.g. hexane, heptane, benzene, methylbenzene, dimethylbenzene and the like; an alcohol, e.g. methanol, ethanol, 2-propanol, 1-butanol and the like; and ether, e.g. 1,1'-oxybisethane, tetrahydrofuran, 1,4-dioxane and the like; a halogenated hydrocarbon, e.g. tetrachloromethane, trichloromethane, dichloromethane and the like; a dipolar aprotic solvent; e.g. N,N-dimethylformamide, N,N-dimethylacetamide, dimethyl sulfoxide, acetonitrile and the like. In some instances, it may be appropriate to conduct the reaction at elevated temperatures. If desired, the anion $W^1$ in the products obtained according to the above procedures can be exchanged for another anion thus obtaining the other quaternay salts of formula (I-q). Such anion-exchange reaction can conveniently be performed following art-known procedures, e.g. by using an anionic exchanger column, or by converting the quaternary imidazolium salt into the corresponding hydroxide with a basic anion exchanger and subsequently reacting said hydroxide with the appropriate acid.

The N-oxides of the compounds of formula (I) can conveniently be prepared by N-oxidating a compound of formula (I). Said N-oxidation reaction may generally be carried out by reacting the starting material of formula (I) with an appropriate organic or inorganic peroxide.

Appropriate inorganic peroxides comprise, for example, hydrogen peroxide, alkali metal or earth alkaline metal peroxides, e.g. sodium peroxide, potassium peroxide, barium peroxide and the like; appropriate organic peroxides may comprise peroxy acids such as, for example, benzenecarboperoxic acid or halo substituted benzenecarboperoxoic acid, e.g. 3-chlorobenzenecarboperoxoic acid and the like, peroxoalkanoic acids, e.g. peroxoacetic acid and the like, alkylhydroperoxides, e.g. t.butyl hydroperoxide and the like. If desired, said N-oxidation may be carried out in a suitable solvent such as, for example, water, a lower alkanol, e.g. methanol, ethanol, propanol, butanol and the like, a hydrocarbon, e.g. benzene, methylbenzene, dimethylbenzene and the like, a ketone, e.g. 2-propanone, 2-butanone and the like, a halogenated hydrocarbon, e.g. dichloromethane, trichloromethane and the like, and mixtures of such solvents. In order to enhance the reaction rate, it may be appropriate to heat the reaction mixture.

The compounds of formula (I) can also be converted into each other following art-known procedures of functional group transformation reactions. Some examples will be cited hereinafter.

A nitro substituent may be introduced on the aromatic part of the bicyclic ring system by art known nitration procedures such as, for example, stirring in a nitric acid solution. Said nitro substituent may, if desired, be further converted into the corresponding amine by art-known nitro-to-amino procedures, e.g. by treating said compounds with hydrogen in the presence of a suitable catalyst such as, for example, platinum-on-charcoal, palladium-on-charcoal and the like catalysts. The hydrogen atom(s) of the amino subtituent may further be replaced by a suitable substituent following art-known procedures such as, for example, reductive N-alkylation and acylation.

A halo substituent may also be introduced on the aromatic part of the bicyclic ring system by art known halogenation procedures, for example, stirring in the presence of bromine in a suitable solvent. Said halo substituents may, if desired, be replaced by a cyano substituent by stirring in the presence of copper (I) cyanide. Y being —CH$_2$S— may be converted to the corresonding sulfoxide or sulfon by an appropriate oxidation procedure, e.g. with a peroxide or a perchlorate.

The substituent R$^2$ on the carboxylic acid group may be transformed to other substituents encompassed by the definition of R$^2$ by convenient reactions known in the art for the modification of carboxylic acid functions, e.g. by hydrolysis and esterification and/or transesterification.

If the synthesis of sterochemically pure isomers is intended, streoselective reaction steps and conditions are recommended. On the other hand conventional methods of separation can be used for obtaining pure isomers from a mixture of stereochemnical isomers.

The starting materials for the preparation of the novel compounds of formula (I) are known, or they can be obtained by known synthesis procedures.

For example, the compounds of formula (II) can be obtained by reacting a glycine ester of formula

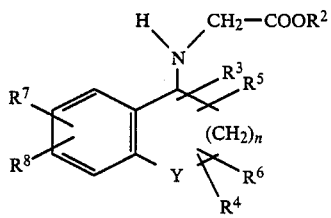

wherein R$^2$, R$^3$, R$^4$, R$^5$, R$^6$, R$^7$, R$^8$, n and Y are as defined hereinabove, with formice acid in the presence of acetic anhydride. In turn, the compounds of formula (IV) can be prepared by reacting an amine of formula

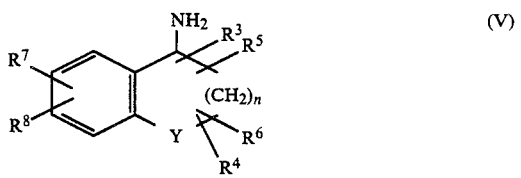

wherein R$^2$, R$^3$, R$^4$, R$^5$, R$^6$, R$^7$, R$^8$, n and Y are as defined under formula (I), with a α-haloacetic acid ester, e.g. α-bromoacetic acid ester, of formula Br—CH$_2$—COOR$^2$ (VI)

The amines of formula (V) can be obtained from carbonyl compounds of formula

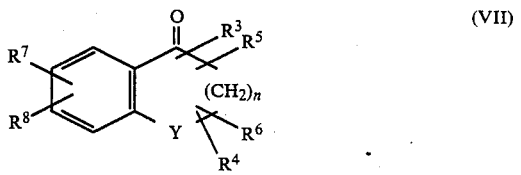

wherein R$^3$, R$^4$, R$^5$, R$^6$, R$^7$, R$^8$, n and Y are as defined under formula (I), by reacting them with hydroxylamine NH$_2$OH, and by hydrogenation of the resulting intermediates of formula

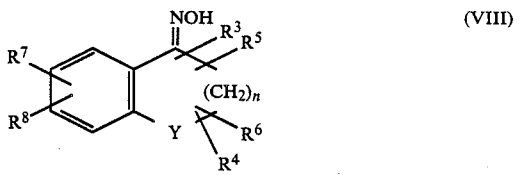

wherein R$^3$, R$^4$, R$^5$, R$^6$, R$^7$, R$^8$, n and Y are as defined under formula (I), with hydrogen in the presence of a hydrogenating noble metal catalyst. The compounds of formula (V) are also obtained by catalytic reduction of (VII) in the presence of ammonia under pressure.

The compounds of formula (I) are stable compounds and no precautionary measures are required for handling them.

When used as the indicated rates of application, the compounds of formula (I) have good selective herbicidal properties which make them most suitable for use in crops of useful plants, preferably in maize and in rice. In some cases damage is also caused to weeds which have only been controlled up to now with total herbicides.

At higher rates of application, all tested plants are so severely damaged in their development that they die.

The invention also relates to heribicidal conditions containing one or more inert carriers and, if desired, other adjuvants and as active ingredient a herbicidally effective amount of a compound of formula (I) as defined hereinabove. Further the invention relates to methods of controlling weeds by the application of the novel compounds.

In the method for controlling weeds according to the invention the compounds of formula (I) are used in unmodified form or, preferably, together with the adjuvants conventionally employed in the art of formulation. They are therefore formulated following art-known procedures to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusing, scattering or pouring, are chosen in accordance with the intended objectives and the prevailing circumstances.

The formulations, i.e. the compositions, preparations or mixtures containing the compound (active ingredient) of formula (I) and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-purrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregrandulated materials of inorganic or organic nature can be used, e.g. especially dolomite or pulverised plant residues.

Depending on the nature of the compound of formula (I) to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, earth alkaline metal salts or unsubstituted or substituted ammonium salts and contain a $C_8$–$C_{22}$ alkyl radial which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylmaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ester groups and 8 to 20 carbon atoms in the (alifatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$ alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981, M. and J. Ash, "Encyclopedia of Surfactants", Vol. I–III, Chemical Publishing Co., N.Y., 1080–81.

The herbicidal compositions which are preferably employed in the method of the invention usually contain 0.1 to 95%, preferably 0.1 to 80%, of a compound of formula (I), 1 to 99%, of a solid or liquid adjuvant, and 0 to 25%, preferably 0.1 to 25%, of a surfactant.

Preferred formulations are composed in particular of the following constituents (%=percentage by weight):

Emulsifiable concentrates
active ingredient: 1 to 20%, preferably 5 to 10%
surfactant: 5 to 30%, preferably 10 to 20%
liquid carrier: 50 to 94%, preferably 70 to 85%

Dusts
active ingredient: 0.1 to 10%, preferably 0.1 to 1%
solid carrier: 99.9 to 90%, preferably 99.9 to 99%

Suspension concentrates
active ingredient: 5 to 75%, preferably 10 to 50%
water: 94 to 25%, preferably 88 to 30%
surfactant: 1 to 40%, preferably 2 to 30%

Wettable powders
active ingredient: 0.5 to 90%, preferably 1 to 80%
surfactant: 0.5 to 20%, preferably 1 to 15%
solid carrier: 5 to 95%, preferably 15 to 90%

Granulates
active ingredient: 0.5 to 30%, preferably 3 to 15%
solid carrier: 99.5 to 70%, preferably 97 to 85%

The following examples are intended to illustrate and not to limit the scope of the present invention. Unless otherwise stated all parts therein are by weight.

(A) PREPARATORY EXAMPLES

Example 1

(a) A mixture of 220 parts of 1-(5-fluoro-2-hydroxy)ethanone, 125 parts of 3-methyl-2-butanone, 53 parts of pyrrolidine and 396 parts of methylbenzene was stirred first for 3 days at room temperature and then for 4 hours at reflux using a water separator. After cooling, the reaction mixture was washed with a sodium hydroxide solution. The precipitated product was filtered off and set aside. From the filtrate, the organic layer was washed with a hydrochloric acid solution, dried, filtered and evaporated. The residue and the precipitated product, which was set aside (see above) were taken up in methanol and activated charcoal was added. The whole was filtered over diatomaceous earth and the filtrate was evaporated. The residue was purified by column chromatography over silica gel using trichloromethane as eluent. The pure fractions were collected and the eluent was evaporated. The residue was distilled, yielding 66 parts (20.5%) of 6-fluoro-2,3-dihydro-2-methyl-2-(1-methylethyl)-4H-1-benzopyran-4-one; bp. 95°–105° C. at 13.30 Pa.

(b) To a stirred mixture of 66 parts of 6-fluoro-2,3-dihydro-2-methyl-2-(1-methylethyl)-4H-1-benzopyran-4-one, 30 parts of hydroxylamine hydrochloride, 128 parts of ethanol and 160 parts of water were added 36 parts of sodium carbonate at 60° C. The reaction mixture was stirred and refluxed over weekend. 160 Parts of water were added. After cooling, dichloromethane was added and the whole was filtered over diatomaceous earth. The organic layer was dried, filtered and evaporated. The residue was taken up in methylbenzene and the latter was evaporated, yielding 68 parts (95.5%) of (E+Z)-6-fluoro-2,3-dihydro-2-methyl-2-(1-methylethyl)-4H-1-benzopyran-4-one, oxime.

(c) A mixture of 68 parts of (E+Z)-6-fluoro-2,3-dihydro-2-methyl-2-(1-methylethyl)-4H-1-benzopyran-4-one, oxime and 400 parts of methanol saturated with ammonia was hydrogenated at normal pressure and at room temperature with 5 parts of Raney-nickel catalyst. After the calculated amount of hydrogen was taken up, the catalyst was filtered off and the filtrate was evaporated. The residue was taken up in dichloromethane and activated charcoal was added. The whole was filtered over diatomaceous earth. From the filtrate, the organic layer was separated, dried, filtrate and evaporated. The residue was taken up in 1,1'-oxybisethane and gaseous hydrogen chloride was bubbled through the solution. The precipitate was filtered off and taken up in a mixture of water and dichloromethane. The whole was made alkaline with a sodium hydroxide solution. The separated organic layer was dried, filtered and evaporated, yielding 44 parts (70.4%) of (cis+trans)-6-fluoro-2,3-dihydro-2-methyl-2-(1-methylethyl)-4H-1-benzopyran-4-amine as a residue (compound 10.34).

(d) A mixture of 44 parts of (cis+trans)-6-fluoro-2,3-dihydro-2-methyl-2-(1-methylethyl)-4H-1-benzopyran-4-amine, 19.7 parts of methyl chloracetate, 21 parts of N,N-diethylethamine and 31.5 parts of N,N-dimethylformamide was stirred overnight at room temperature. After the addition of 1,1'-oxybisethane, the precipitate was filtered and the filtrate was washed four times with water, dried, filtered and evaporated. The residue was purified by column chromatography over silica gel using trichloromethane as eluent. The pure fractions were collected and the eluent was evaporated, yielding 50 parts (84.6%) of methyl (cis+trans)-N-[6-fluoro-2,3-dihydro-2-methyl-2-(1-methylethyl)-4H-1-benzopyran-4-yl]glycine as a residue (compound 9.37).

(e) A mixture of 50 parts of methyl (cis+trans)-N-[6-fluoro-2,3-dihydro-2-methyl-2-(1-methylethyl)-4H-1-benzopyran-4yl]glycine, 9.6 parts of formic acid and 54 parts of dimethylbenzene was stirred and refluxed for 5 hours using a water separator (formic acid was added a few times). After cooling, the reaction mixture was washed successively with a formic acid solution 20%, a sodium carbonate solution and twice with a sodium chloride solution. Crystallization occured after the last washing, whereupon dichloromethane was added. The organic layer was dried, filtered and evaporated. The residue was crystallized from 2,2'-oxybispropane. The product was filtered off and dried in vacuo at 40° C., yielding 30 parts (54.6%) iof methyl (cis+trans)-N-[6-fluoro-2,3-dihydro-2-methyl-2-(1-methylethyl)-4H-1-benzopyran-4yl]-N-formylglycine; mp. 115.4° C. (compound 8.37).

(f) To a stirred mixture of 28 parts of methyl (cis+trans)-N[6-fluoro-2,3-dihydro-2-methyl-2-(1-methylethyl)-4H-1-benzopyran-4yl]-N-formylglycine and 216 parts of tetrahydofuran were added portionwise 4.2 parts of a sodium hydride dispersion 50%, followed by the addition of 16.5 parts of methyl formate. Stirring was continued for 1 day at reflux (a few parts of methanol were added). The reaction mixture was evaporated. The residue was taken up in a mixture of 1,1'-oxybisethane and water. The aqueous phase was acidified with hydrochloric acid and extracted with dichloromethane. The organic layer was dried, filtered and evaporated. 68 Parts of methanol, 22.8 parts of concentrated hydrochloric acid, 35 parts of water and 13.1 parts of potassium thiocyanate in 15 parts of water were added to the residue. The mixture was stirred overnight at 60° C. The product was extracted with dichloromethane. The extract was dried (activated charcoal), filtered and evaporated. The residue was purified by column chromatography over silica gel using a mixture of trichloromethane and methanol (99:1 by volume) as eluent. The pure fractions were collected and the eluent was evaporated, yielding 28 parts (88.3%) of methyl (cis+trans)-1-[6-fluoro-2,3-dihydro-2-methyl-2-(1-methylethyl)-4H-1-benzopyran-4-yl]-2-mercapto-1H-imidazole-5-carboxylate as a residue (compound 1.58)

A mixture of 28 parts of methyl (cis+trans)-1-[6-fluoro-2,3-dihydro-2-methyl-2-(1-methylethyl)-4H-1-benzopyran-4-yl]-2-mercapto-1H-imidazole-5-carboxylate, 75 parts of water, 30 parts of nitric acid and 0.1 parts of sodium nitrate was stirred for 2.50 hours at room temperature. The reaction mixture was poured into water and dichloromethane. The whole was made alkaline with a sodium hydroxide solution in an ice bath. The mixture was filtered over diatomaceous earth and from the filtrate, the organic layer was dried, filtered and evaporated. The residue was purified by column chromatography over silica gel using a mixture of trichloromethane and methanol (99:1 by volume) as eluent. The pure fractions were collected and the eluent was evaporated. The residue was further purified by column chromatography (HPLC) over silica gel using a mixture of methylbenzene and ethanol (97:3 by volume) as eluent. The pure fractions were collected and the eluent was evaporated. The residue was converted into the nitrate salt in 2-propanone, 1,1'-oxybisethane and 2,2'-oxybispropane. The salt was filtered off and dried in vacuo at 55° C., yielding 14.4 parts (47.3%) of methyl (cis+trans)-1-[6-fluoro-2,3-dihydro-2-methyl-2-(1-methylethyl)-4H-1-benzopyran-4yl]-1H-imidazole-5-carboxylate mononitrate; mp. 124.6° C. (compound 1.126).

Example 2

There were also obtained methyl (trans)-1-(2,3-dihydro-2-methyl-4H-1-benzopyran-4-yl)-1H-imidazole-5-carboxylate mononitrate hemihydrate; mp. 139.0° C. (compound 1.73) and methyl(cis)-1-(2,3-dihydro-2-methyl-4H-1-benzopyran-4-yl)-1H-imidazole-5-carboxylate mononitrate; mp. 147.3° C. (compound 1.76) Said pure isomers were prepared by separating a mixture of methyl (trans)-N-(2,3-dihydro-2-methyl-4H-1-benzopyran-4-yl)glycine and (cis)-N-(2,3-dihydro-2-methyl-4H-1-benzopyran-4yl)glycine by column chromatography over silica gel using a mixture of trichloromethane and methanol (99:1 by volume) as eluent and further purifying the residues by column chromatography (HPLC) over silica gel using a mixture of dichloromethane and 2-propanol (97.5:2.5 by volume) as eluent, and condensing both obtained isomers following the same procedures as described above in example 1.

Example 3

33.0 Parts of ammonium carbonate are added at room temperature to a solution of 19.3 parts of methyl 2-[(2,3-dihydro-2,2,6-trimethyl-4H-1-benzopyran-4yl)formylamino]-3-oxopropanoate in 260 parts of dimethylbenzene. The mixture is heated to 70° C. for 1 hour, then the temperature is raised to 120° C. for 3 hours. After concentration, methyl 1-(2,3-dihydro-2,2,6-trimethyl-4H-1-benzopyran-4yl)-1H-imidazole-5-carboxylate precipitates from the solution, having a melting point of 100°~101° C. (compound 1.13).

Example 4

A mixture of 19.3 parts of methyl 2-[(2,3-dihydro-2,2,6-trimethyl-4H-1-benzopyran-4yl)formylamino]-3-oxopropanoate, 65.0 parts of ammonium acetate and 100 parts of acetic acid is refluxed for 8 hours. Then additional 50 parts of ammonium acetate are added and the refluxing is continued for further 4 hours. The solution is diluted with 300 parts of water and extracted twice with 90 parts of methylbenzene each time. The organic phases are combined, concentrated and separated at silica gel by chromatography. Concentration of the eluant yields methyl 1-(2,3-dihydrio-2,2,6-trimethyl-4H-1-benzopyran-4yl)-1H-imidazole-5-carboxylate, having a melting point of 100°~101° C. (compound 1.13).

Example 5

A mixture of 16.5 parts of methyl 2-[(2,3-dihydro-2,2,6-trimethyl-4H-1-benzopyran-4-yl)formylamino]-3-oxopropanoate, 58 parts of formamide and 12 parts of hydrochloric acid are heated to 140° C. for 8 hours. After cooling to room temperature, the mixture is extracted with a mixture of 100 parts of water and 70 parts of 1,1'-oxybisethane. The ethanol phase is separated and the aqueous phase is extracted twice with 70 parts of 1,1'-oxybisethane each time. The combined organic phases are dried over sodium sulfate and concentrated to dryness. The residue is crystallized, yielding pure methyl 1-(2,3-dihydro-2,2,6-trimethyl-4H-1-benzopyran-4yl)-1H-imidazole-5-carboxylate with a melting point of 100°~101° C. (compound 1.13).

Example 6

A solution of 31 parts of methyl 1-(8-chloro-2,3-dihydro-4H-1-benzopyran-4-yl)-1H-imidazole-5-carboxylate mononitrate in 260 parts of a nitric acid solution 60% was stirred for 45 minutes at room temperature (exothermic reaction). The reaction mixture was poured into crushed ice and the whole was made alkaline. The product was extracted with trichloromethane. The undissolved product was filtered off (the trichloromethane layer was set aside) and dried, yielding a first fraction of 7 parts (20.0%) of methyl 1-(8-chloro-2,3-dihydro-6-nitro-4H-1-benzopyran-4-yl)-1H-imidazole-5-carboxylate mononitrate. The trichloromethane layer, which was set aside (see above), was washed with water, dried, filtered and evaporated. The residue was converted into the nitric acid salt. The product was filtered off and dried, yielding a second fraction of 21 parts (60.2%) of methyl 1-(8-chloro-2,3-dihydro-6-nitro-4H-1-benzopyran-4-yl)-1H-imidazole-5-carboxylate mononitrate.

Total yield: 28 parts (80.2%) of methyl 1-(8-chloro-2,3-dihydro-6-nitro-4H-1-benzopyran-4yl)-1H-imidazole-5-carboxylate mononitrate (compound 1.62).

Example 7

A mixture of 48 parts of methyl 1-(8-chloro-2,3-dihydro-6-nitro-4H-1-benzopyran-4-yl)-1H-imidazole-5-carboxylate, 8 parts of calcium oxide and 400 parts of methanol was hydrogenated at normal pressure and at room temperature with 2 parts of palladium-on-charcoal catalyst 5%. After the calculated amount of hydrogen was taken up, the catalyst was filtered off and the filtrate was evaporated. The residue was taken up in trichloromethane. The organic layer was washed with water and evaporated. The residue was purified by column chromatography over silica gel using a mixture of trichloromethane and methanol (90:10 by volume) as eluent. The pure fractions were collected and the eluent was evaporated. The residue was converted into the hydrochloride salt in a mixture of 2-propanol and 2,2'-oxybispropane. The salt was filtered off and salt overnight in vacuo at 80° C., yielding 18.3 parts (35.3%) of methyl 1-(6-amino-2,3-dihydro-4H-1-benzopyran-4-yl)-1H- imidazole-5-carboxylate monohydrochloride.2-propanolate (1:1); mp. 146.0° C. (compound 1.135).

Example 8

To a stirred solution of 2.8 parts of methyl 1-(6-amino-2,3-dihydro-4H-1-benzopyran-4-yl)-1H-imidazole-5-carboxylate in 50 parts of acetic acid were added 4 parts of acetic acid anhydride. The whole was stirred overnight at room temperature. After evaporation in vacuo, the residue was taken up in trichloromethane. The solution was washed with a sodium hydroxide solution 5%. The organic layer was evaporated and the residue was converted into the nitrate salt in 2-propanone. The salt was filtered off and dried in vacuo, yielding 3.4 parts (44.9%) of methyl 1-[6-(acetylamino)-2,3-dihydro-4H-1-benzopyran-4-yl]-1H-imidazole-5-carboxylate mononitrate; mp. 159.3° C. (compound 1.136).

Example 9

A mixture of 4.4 parts of methyl 1-(6-amino-2,3-dihydro-4H-1-benzopyran-4-yl)-1H-imidazole-5-carboxylate monohydrochloride, 4 parts of poly(oxymethylene), 2 parts of potassium acetate and 200 parts of methanol was hydrogenated at normal pressure and at 50° C. with 2 parts of palladium-on-charcoal catalyst 10%. After the calculated amount of hydrogen was taken up, the catalyst was filtered off and the filtrate was evaporated. The residue was taken up in trichloromethane. The organic layer was washed with a sodium hydrogen carbonate solution and water, dried, filtered and evaporated. The residue was converted into the hydrochloride salt in 2-propanol. The salt was filtered off and dried in vacuo at 70° C., yielding 3.3 parts (73.4%) of methyl 1-[6-(dimethylamino)-2,3-dihydro-4H-1-benzopyran-4-yl]-1H-imidazole-5-carboxylate dichloride; mp. 163.5° C. (compound 1.137).

Example 10

To a stirred solution of 6.0 parts of methyl 1-[3,4-dihydrospiro-[2H-1-benzopyran-2,1'-cyclopentan]-4-yl]-1H-imidazole-5-carboxylate mononitrate in 135 parts of methanol were added 3.2 parts of bromine. The mixture was stirred for 1 hour at room temperature. The reaction mixture was poured into water and the whole was made alkaline. The product was extracted with 1,1'-oxybisethane. The extract was dried, filtered and evaporated. The residue was converted into the nitrate salt in a mixture of 16 parts of 2-propanone and 40 parts of 2,2'-oxybispropane. The salt was filtered off and dried in vacuo, yielding 4.4 parts (48.4%) of methyl 1-(6-bromo-3,4-dihydrospiro-[2H-1-benzopyran-2,1'-cyclopentan]-4-yl)-1H-imidazole-5-carboxylate mononitrate; mp. 162.3° C. (compound 1.63).

Example 11

To a solution of 32 parts of methyl 1-(6-bromo-2,3-dihydro-4H-1-benzopyran-4-yl)-1H-imidazole-5-carboxylate in 90 parts of N,N-dimethylformamide were added 8.6 parts of copper(I) cyanide. The whole was stirred overnight at reflux temperature. The reaction mixture was poured into 350 parts of a sodium cyanide solution 10% in water and the whole was stirred for 1 hour at 60° C. The product was extracted with methylbenzene. The extract was dried, filtered and evaporated. The residue was purified by column chromatography (HPLC) over silica gel using a mixture of hexane and methyl acetate (85:15 by volume) as eluent. The pure fractions were collected and the eluent was evaporated. The residue was converted into the nitrate salt in 2-propanone and 2,2'-oxybispropane. The salt was filtered off and dried, yielding 7 parts (20.2%) of methyl 1-(6-cyano-2,3-dihydro-4H-1-benzopyran-4-yl)-1H-imidazole-5-carboxylate mononitrate; mp. 169.6° C. (compound 1.147).

Example 12

A solution of 80 parts of methyl 1-(2,3-dihydro-2,2-methyl-4H-1-benzopyran-4-yl)-1H-imidazole-5-carboxylate mononitrate and 80 parts of a sodium hydroxide solution 50% in 200 parts of water was stirred for 2 hours at reflux temperature. After cooling, the reaction mixture was neutralized with acetic acid and the product was allowed to crystallize. The crystallized product was filtered off, washed twice with water and dried in vacuo at 80° C., yielding 52 parts (82%) of 1-(2,3-dihydro-2,2-dimethyl-4H-1-benzopyran-4-yl)-1H-imidazole-5-carboxylic acid; mp. 245.5° C. (compound 1.132).

Example 13

A solution of 3.3 parts of 1-(2,3-dihydro-2,2-dimethyl-4H-1-benzopyran-4-yl)-1H-imidazole-5-carboxylic acid in 45 parts in warm N,N-dimethylformamide was cooled to room temperature and then 2 parts of 1,1'-carbonylbis[1H-imidazole] were added. The whole was stirred at room temperature till $CO_2$ evolution had ceased (±30 minutes). The mixture was heated to ±70° C. and 2.4 parts of ethanol and 0.1 parts of sodium ethoxide were added. Stirring was continued over weekend at ±70° C. After evaporation, the residue was taken up in water and trichloromethane. The organic layer was washed with water, dried, filtered and evaporated. The residue was purified by column chromatography over silica gel using trichloromethane as eluent. The pure fractions were collected and the eluent was evaporated. The residue was crystallized from hexane. The product was filtered off and dried, yielding 2.36 parts (63.5%) of ethyl 1-(2,3-dihydro-2,2-dimethyl-4H-1-benzopyran-4-yl)-1H-imidazole-5-carboxylate; mp. 80.9° C. (compound 1.138).

Example 14

3.3 Parts of 1-(2,3-dihydro-2,2-dimethyl-4H-1-benzopyran-4-yl)-1H-imidazole-5-carboxylic acid were dissolved in 45 parts of warm N,N-dimethylformamide. After cooling to room temperature, 2 parts of 1,1'-carbonylbis[1H-imidazole] were added and the whole was stirred for 1 hour at this temperature. The whole was heated to ±80° C. and a mixture of 0.1 parts of a cyclohexanol sodium salt solution and 3 parts of cyclohexanol was added. After stirring for 5 days at ±80° C., the mixture was evaporated. The residue was taken up trichloromethane and water and the organic layer was dried, filtered and evaporated. The residue was purified by column chromatography over silica gel using trichloromethane as eluent. The pure fractions were collected and the eluent was evaporated. The residue was crystallized from hexane. The product was filtered off and dried, yielding 0.91 parts (20.5%) of cyclohexyl 1-(2,3-dihydro-2,2-dimethyl-4H-1-benzopyran-4-yl)-1H-imidazole-5-carboxylate; mp. 128.1° C. (compound 1.139).

Example 15

A solution of 4.2 parts of methyl trans-1-(2,3-dihydro-2-methyl-4H-1-benzopyran-4-yl)-1H-imidazole-5-carboxylate and 12 parts of iodomethane in 65 parts of dichloromethane is stirred for 20 hours at room temperature. The reaction mixture is evaporated and the residue is crystallized twice from 2,2'-oxybispropane. The product is filtered off and dried, yielding trans-1-(2,3-dihydro-2-methyl-4H-1-benzopyran-4-yl)-5-(methoxycarbonyl)-3-methyl-1H-imidazolium iodide (compound 7.04).

Example 16

To a stirred and cooled (0° C.) solution of 5.4 parts of methyl trans-1-(2,3-dihydro-2-methyl-4H-1-benzopyran-4-yl)-1H-imidazole-5-carboxylate in 130 parts of dichloromethane are added 3.4 parts of 3-chlorobenzenecarboperoxoic acid. After stirring for 24 hours at room temperature, the reaction mixture is washed with 100 parts of a solution of sodium hydrogen carbonate in water (0.03M) and water, dried, filtered and evaporated (<30° C.) The residue is purified by column chromatography over silica gel using a mixture of trichloromethane and methanol, saturated with ammonia (95:5 by volume) as eluent. The pure fractions are collected and the eluent is evaporated. The residue is crystallized from hexane. The product is filtered off and dried, yielding methyl trans-1-(2,3-dihydro-2-methyl-4H-1-benzopyran-4-yl)-1H-imidazole-5-carboxylate, $N^3$-oxide (compound 7.101).

Example 17

To a stirred solution of 11 parts of sodium methoxide in 135 parts of tetrahydrofuran were added successively 40 parts of methyl formate and 53 parts of methyl 2-[(3,4-dihydro-2H-1-benzothiopyran-4-yl)-formylamino]acetate. The whole was stirred for 18 hours at room temperature. Upon cooling 300 parts of water were added. The aqueous phase was separated and 48 parts of a hydrochloric acid solution (conc.) and 160 parts of methanol were added. Then a solution of 20 parts of potassium isothiocyanate in 30 parts of water was added and the whole was stirred overnight at room temperature. The precipitated product was filtered off and crystallized a few times from 2-propanol, yielding 14 parts of (22%) of methyl 1-(3,4-dihydro-2H-1-benzothiopyran-4-yl)-2-mercapto-1H-imidazole-5-carboxylate; mp. 163.3° C. (compound 2.02).

Compound 2.02 (5 g) is stirred in 240 parts of methanol saturated with ammonia. To this solution is added 20 parts of Raney-nickel and the whole is heated to 70° C. during 14 hours. The catalyst is filtered off and washed with hot ethanol. The combined filtrates are concentrated in vacuo and the residue is purified over silica gel using trichloromethane and methanol (95:5 by volume) as eluent. The pure fractions are collected and the eluent is evaporated, yielding methyl 1-(3,4-dihydro-2H-1-benzothiopyran-4-yl)-1H-imidazole-5-carboxylate (compound 2.01) as a residue.

All other compounds and intermediates listed in the Tables 1 to 10 can be obtained by analogous methods of preparation.

TABLE 1a

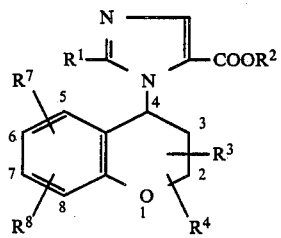

| comp. No. | $R^1$ | $R^2$ | $R^3$ | $R^4$ | $R^7$ | $R^8$ | physical data |
|---|---|---|---|---|---|---|---|
| 1.01 | H | $CH_3$ | H | H | H | H | .$HNO_3$/mp. 152.5–153.5° C. |
| 1.02 | H | $CH_3$ | H | H | H | H | mp. 82.2° C. |
| 1.03 | H | $CH_3$ | H | H | 6-F | H | .$HNO_3$/mp. 155.4° C. |
| 1.04 | H | $CH_3$ | 2-$CH_3$ | 2-$CH_3$ | H | H | .$HNO_3$/mp. 160.1° C. |
| 1.05 | H | $CH_3$ | H | H | 6-Br | H | .$HNO_3$/mp. 154.7° C. |
| 1.06 | H | $CH_3$ | H | H | 8-Cl | H | .$HNO_3$/mp. 189.9° C. |
| 1.07 | H | $CH_3$ | 2-$(CH_2)_4$—2 | | 7-F | H | |
| 1.08 | H | $CH_3$ | 2-$(CH_2)_4$—2 | | H | H | .$HNO_3$/mp. 140.8° C. |
| 1.09 | H | $CH_3$ | 2-$(CH_2)_5$—2 | | H | H | .$HNO_3$/mp. 175.6° C. |
| 1.10 | H | $CH_3$ | 2-$C_6H_5$ | H | H | H | mp. 160.3° C. |
| 1.11 | H | $CH_3$ | 2-$C_6H_5$ | 2-$CH_3$ | H | H | .$HNO_3$ |
| 1.12 | H | $CH_3$ | 2-$C_3H_7$—i | 2-$CH_3$ | H | H | .$HNO_3$/mp. 130.9° C. |
| 1.13 | H | $CH_3$ | 2-$CH_3$ | 2-$CH_3$ | 6-$CH_3$ | H | mp. 100–101° C. |
| 1.14 | H | $CH_3$ | 2-$(CH_2)_4$—2 | | 7-$CH_3$ | H | mp. 134° C. (dec.) |
| 1.15 | H | $CH_3$ | 2-$(CH_2)_4$—2 | | 7-$CH_3$ | H | $HNO_3$/mp. 183° C. (dec.) |
| 1.16 | H | $CH_3$ | 2-$(CH_2)_4$—2 | | 6-$OCH_3$ | H | mp. 138° C. (dec.) |
| 1.17 | H | $CH_3$ | 2-$(CH_2)_4$—2 | | 6-$OCH_3$ | H | .$HNO_3$/mp. 183° C. |
| 1.18 | H | $CH_3$ | 3-$CH_3$ | 3-$CH_3$ | 7-$CH_3$ | H | resin |
| 1.19 | H | $CH_3$ | 3-$CH_3$ | 3-$CH_3$ | H | H | mp. 104–106° C. |
| 1.20 | H | $CH_3$ | 3-$CH_3$ | H | H | H | |
| 1.21 | H | $C_2H_5$ | H | H | H | H | |
| 1.22 | H | $C_4H_9$—n | H | H | H | H | |
| 1.23 | H | $C_3H_7$—i | H | H | H | H | |
| 1.24 | H | $C_2H_5$ | 2-$CH_3$ | 2-$CH_3$ | 7-$CH_3$ | H | |
| 1.25 | SH | $CH_3$ | 2-$CH_3$ | 2-$CH_3$ | 6-$CH_3$ | H | mp. 171–172° C. |
| 1.26 | SH | $CH_3$ | 2-$C_6H_5$ | H | H | H | mp. 120.4° C. |
| 1.27 | SH | $CH_3$ | 2-$(CH_2)_4$—2 | | 7-$CH_3$ | H | mp. 184–185° C. |
| 1.28 | SH | $CH_3$ | 2-$CH_3$ | 2-$CH_3$ | 7-$CH_3$ | H | mp. 164–165° C. |
| 1.29 | SH | $CH_3$ | 2-$(CH_2)_4$—2 | | H | H | mp. 165.9° C. |
| 1.30 | SH | $CH_3$ | 2-$(CH_2)_4$—2 | | 6-$OCH_3$ | H | mp. 162–163° C. |

TABLE 1a-continued

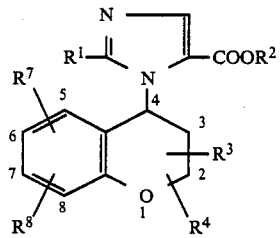

| comp. No. | R¹ | R² | R³ | R⁴ | R⁷ | R⁸ | physical data |
|---|---|---|---|---|---|---|---|
| 1.31 | H | CH$_2$—CH=CH$_2$ | H | H | 6-Cl | 8-Cl | |
| 1.32 | SH | CH$_2$—CH=CH$_2$ | H | H | 6-Cl | 8-Cl | |
| 1.33 | H | CH$_2$—C≡CH | H | H | H | H | |
| 1.34 | SH | CH$_2$—C≡CH | H | H | H | H | |
| 1.35 | H | CH$_3$ | 2-CH$_3$ | 2-CH$_3$ | 6-CH$_3$ | 8-CH$_3$ | |
| 1.36 | SH | CH$_3$ | 2-CH$_3$ | 2-CH$_3$ | 6-CH$_3$ | 8-CH$_3$ | |
| 1.37 | H | C$_2$H$_5$ | | 2-(CH$_2$)$_4$—2 | 5-Cl | 7-Cl | |
| 1.38 | SH | C$_2$H$_5$ | | 2-(CH$_2$)$_4$—2 | 5-Cl | 7-Cl | |
| 1.39 | SH | C$_2$H$_5$ | | 2-(CH$_2$)$_3$—2 | H | H | |
| 1.40 | H | C$_2$H$_5$ | | 2-(CH$_2$)$_3$—2 | H | H | |
| 1.41 | H | CH$_3$ | | 2-(CH$_2$)$_2$—2 | H | H | |
| 1.42 | SH | CH$_3$ | | 2-(CH$_2$)$_2$—2 | H | H | |
| 1.43 | H | C$_2$H$_5$ | | 2-(CH$_2$)$_5$—2 | 5-Cl | 7-OCH$_3$ | |
| 1.44 | SH | C$_2$H$_5$ | | 2-(CH$_2$)$_5$—2 | 5-Cl | 7-OCH$_3$ | |
| 1.45 | H | C$_3$H$_7$—n | | 2-(CH$_2$)$_6$—2 | H | H | |
| 1.46 | SH | C$_3$H$_7$—n | | 2-(CH$_2$)$_6$—2 | H | H | |
| 1.47 | SH | CH$_3$ | H | H | H | H | mp. 201–202.5° C. |
| 1.48 | SH | CH$_3$ | H | H | 6-F | H | |
| 1.49 | SH | CH$_3$ | 2-CH$_3$ | 2-CH$_3$ | H | H | oil |
| 1.50 | SH | CH$_3$ | H | H | 6-Cl | H | mp. 237.2° C. |
| 1.51 | SH | CH$_3$ | H | H | 6-Br | H | mp. 246.5° C. |
| 1.52 | SH | CH$_3$ | H | H | 8-Cl | H | mp. 192.2° C. |
| 1.53 | SH | CH$_3$ | | 2-(CH$_2$)$_4$—2 | 6-F | H | |
| 1.54 | H | CH$_3$ | | 2-(CH$_2$)$_4$—2 | 6-F | H | .HNO$_3$/mp. 152.0° C. |
| 1.55 | SH | CH$_3$ | | 2-(CH$_2$)$_5$—2 | H | H | |
| 1.56 | H | CH$_3$ | 2-CH$_3$ | 2-C$_2$H$_5$ | H | H | .HNO$_3$/mp. 125.0° C. |
| 1.57 | SH | CH$_3$ | 2-C$_3$H$_7$—i | 2-CH$_3$ | H | H | |
| 1.58 | SH | CH$_3$ | 2-C$_3$H$_7$—i | 2-CH$_3$ | 6-F | H | |
| 1.59 | SH | CH$_3$ | 2-C$_6$H$_{13}$—n | 2-CH$_3$ | 6-F | H | |
| 1.60 | H | CH$_3$ | 2-C$_6$H$_{13}$—n | 2-CH$_3$ | 6-F | H | |
| 1.61 | H | CH$_3$ | H | H | 6-NO$_2$ | H | mp. 145.4° C. |
| 1.62 | H | CH$_3$ | H | H | 6-NO$_2$ | 8-Cl | .HNO$_3$/mp. 186.6° C. |
| 1.63 | H | CH$_3$ | | 2-(CH$_2$)$_4$—2 | 6-Br | H | .HNO$_3$/mp. 162.3 |
| 1.64 | H | CH$_3$ | 2-CH$_3$ | 3-CH$_3$ | H | H | (A + B).HNO$_3$/mp. 144.1° C. |
| 1.65 | SH | CH$_3$ | 3-CH$_3$ | H | H | H | trans/mp. 168.5–169° C. |
| 1.66 | H | CH$_3$ | 3-CH$_3$ | H | H | H | trans/mp. 82–84° C. |
| 1.67 | SH | CH$_3$ | 3-CH$_3$ | H | H | H | cis/mp. 124–126° C. |
| 1.68 | H | CH$_3$ | 3-CH$_3$ | H | H | H | cis/mp. 201.6° C. |
| 1.69 | SH | CH$_3$ | 2-CH$_3$ | H | H | H | |
| 1.70 | H | CH$_3$ | 2-CH$_3$ | H | H | H | .HNO$_3$/mp. 138.8° C. |
| 1.71 | H | H | 2-CH$_3$ | H | H | H | |
| 1.72 | SH | CH$_3$ | 2-CH$_3$ | H | H | H | trans |
| 1.73 | H | CH$_3$ | 2-CH$_3$ | H | H | H | trans/.HNO$_3$.1/2H$_2$O mp. 139.0° C. |
| 1.74 | H | H | 2-CH$_3$ | H | H | H | trans/mp. 258.9° C. |
| 1.75 | SH | CH$_3$ | 2-CH$_3$ | H | H | H | cis/mp. 206.5° C. |
| 1.76 | H | CH$_3$ | 2-CH$_3$ | H | H | H | cis/HNO$_3$/mp. 147.3° C. |
| 1.77 | H | H | 2-CH$_3$ | H | H | H | cis |
| 1.78 | SH | CH$_3$ | 2-CF$_3$ | H | H | H | |
| 1.79 | H | CH$_3$ | 2-CF$_3$ | H | H | H | |
| 1.80 | H | CH$_3$ | 2-CF$_3$ | H | H | H | trans |
| 1.81 | H | CH$_3$ | 2-CF$_3$ | H | H | H | cis |
| 1.82 | SH | CH$_3$ | 2-C$_2$H$_5$ | H | H | H | |
| 1.83 | H | CH$_3$ | 2-C$_2$H$_5$ | H | H | H | |
| 1.84 | H | H | 2-C$_2$H$_5$ | H | H | H | cis/CH$_3$—CH(OH)—CH$_3$ mp. 196.2° C. |
| 1.85 | SH | CH$_3$ | 2-C$_2$H$_5$ | H | H | H | trans/mp. 153° C. |
| 1.86 | H | CH$_3$ | 2-C$_2$H$_5$ | H | H | H | trans/HNO$_3$/mp. 141.3° C. |
| 1.87 | SH | CH$_3$ | 2-C$_2$H$_5$ | H | H | H | cis/mp. 196.5° C. |
| 1.88 | H | CH$_3$ | 2-C$_2$H$_5$ | H | H | H | cis/HNO$_3$/mp. 153.0° C. |
| 1.89 | SH | CH$_3$ | 2-C$_3$H$_7$—n | H | H | H | |
| 1.90 | H | CH$_3$ | 2-C$_3$H$_7$—n | H | H | H | |
| 1.91 | H | H | 2-C$_3$H$_7$—n | H | H | H | |
| 1.92 | SH | CH$_3$ | 2-C$_3$H$_7$—n | H | H | H | trans |
| 1.93 | H | CH$_3$ | 2-C$_3$H$_7$—n | H | H | H | trans/HNO$_3$/mp. 155° C. |
| 1.94 | SH | CH$_3$ | 2-C$_3$H$_7$—n | H | H | H | cis |
| 1.95 | H | CH$_3$ | 2-C$_3$H$_7$—n | H | H | H | cis/mp. 120° C. |
| 1.96 | SH | CH$_3$ | 2-C$_3$H$_7$—i | H | H | H | |
| 1.97 | H | CH$_3$ | 2-C$_3$H$_7$—i | H | H | H | |

TABLE 1a-continued

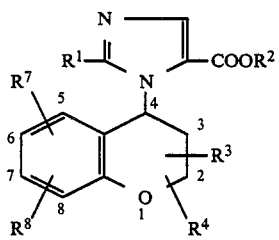

| comp. No. | $R^1$ | $R^2$ | $R^3$ | $R^4$ | $R^7$ | $R^8$ | physical data |
|---|---|---|---|---|---|---|---|
| 1.98 | H | H | 2-$C_3H_7$—i | H | H | H | |
| 1.99 | SH | $CH_3$ | 2-$C_3H_7$—i | H | H | H | trans |
| 1.100 | H | $CH_3$ | 2-$C_3H_7$—i | H | H | H | trans |
| 1.101 | SH | $CH_3$ | 2-$C_3H_7$—i | H | H | H | cis |
| 1.102 | H | $CH_3$ | 2-$C_3H_7$—i | H | H | H | cis |
| 1.103 | SH | $CH_3$ | 2-$C_4H_9$—n | H | H | H | |
| 1.104 | H | $CH_3$ | 2-$C_4H_9$—n | H | H | H | |
| 1.105 | H | H | 2-$C_4H_9$—n | H | H | H | |
| 1.106 | SH | $CH_3$ | 2-$C_4H_9$—n | H | H | H | trans |
| 1.107 | H | $CH_3$ | 2-$C_4H_9$—n | H | H | H | trans |
| 1.108 | SH | $CH_3$ | 2-$C_4H_9$—n | H | H | H | cis |
| 1.109 | H | $CH_3$ | 2-$C_4H_9$—n | H | H | H | cis |
| 1.110 | SH | $CH_3$ | 2-$C_5H_{11}$—n | H | H | H | |
| 1.111 | H | $CH_3$ | 2-$C_5H_{11}$—n | H | H | H | |
| 1.112 | H | H | 2-$C_5H_{11}$—n | H | H | H | |
| 1.113 | SH | $CH_3$ | 2-$C_5H_{11}$—n | H | H | H | trans |
| 1.114 | H | $CH_3$ | 2-$C_5H_{11}$—n | H | H | H | trans |
| 1.115 | SH | $CH_3$ | 2-$C_5H_{11}$—n | H | H | H | cis |
| 1.116 | H | $CH_3$ | 2-$C_5H_{11}$—n | H | H | H | cis |
| 1.117 | SH | $CH_3$ | 2-$C_6H_{13}$—n | H | H | H | |
| 1.118 | H | $CH_3$ | 2-$C_6H_{13}$—n | H | H | H | |
| 1.119 | H | H | 2-$C_6H_{13}$—n | H | H | H | |
| 1.120 | SH | $CH_3$ | 2-$C_6H_{13}$—n | H | H | H | trans |
| 1.121 | H | $CH_3$ | 2-$C_6H_{13}$—n | H | H | H | trans/$HNO_3$/mp. 125.1° C. |
| 1.122 | SH | $CH_3$ | 2-$C_6H_{13}$—n | H | H | H | cis |
| 1.123 | H | $CH_3$ | 2-$C_6H_{13}$—n | H | H | H | cis/$HNO_3$/mp. 151.9° C. |
| 1.124 | SH | $CH_3$ | 2-$CH_3$ | 2-$C_3H_7$—i | 6-F | H | |
| 1.125 | H | $CH_3$ | 2-$CH_3$ | 2-$C_3H_7$—i | 6-F | H | |
| 1.126 | H | $CH_3$ | 2-$CH_3$ | 2-$C_3H_7$—i | 6-F | H | .$HNO_3$/mp. 124.6° C. |
| 1.127 | SH | $CH_3$ | 2-benzyl | H | H | H | |
| 1.128 | H | $CH_3$ | 2-benzyl | H | H | H | .$HNO_3$ |
| 1.129 | SH | $CH_3$ | 3-benzyl | H | H | H | mp. 203.9° C. |
| 1.130 | H | $CH_3$ | 3-benzyl | H | H | H | .$HNO_3$/mp. 147.9° C. |
| 1.131 | H | $CH_3$ | | 2-$(CH_2)_4$—2 | 5-$NO_2$ | 6-$OCH_3$ | mp. 158–160° C. |
| 1.132 | H | H | 2-$CH_3$ | 2-$CH_3$ | H | H | mp. 245.5° C. |
| 1.133 | H | $CH_3$ | H | H | 5-$NH_2$ | H | .HCl |
| 1.134 | H | $CH_3$ | H | H | 5-NH—$COCH_3$ | H | .$HNO_3$ |
| 1.135 | H | $CH_3$ | H | H | 6-$NH_2$ | H | .HCl.2-propanol m.p. 146.0° C. |
| 1.136 | H | $CH_3$ | H | H | 6-NH—$COCH_3$ | H | .$HNO_3$/mp. 159.3° C. |
| 1.137 | H | $CH_3$ | H | H | 6-$N(CH_3)_2$ | H | .2HCl/mp. 163.5° C. |
| 1.138 | H | $C_2H_5$ | 2-$CH_3$ | 2-$CH_3$ | H | H | mp. 80.9° C. |
| 1.139 | H | cyclohexyl | 2-$CH_3$ | 2-$CH_3$ | H | H | mp. 128.1° C. |
| 1.140 | H | $CH_3$ | 2-$CH_3$ | 2-$CH_3$ | 7-$CH_3$ | H | .$HNO_3$/mp. 150° C. (dec.) |
| 1.141 | H | $C_3H_7$—n | 2-$CH_3$ | 2-$CH_3$ | H | H | oil |
| 1.142 | H | $C_3H_7$—i | 2-$CH_3$ | 2-$CH_3$ | H | H | mp. 108.7° C. |
| 1.143 | H | H | | 2-$(CH_2)_4$—2 | H | H | mp. 186.3° C. |
| 1.144 | H | H | | 2-$(CH_2)_4$—2 | 6-Br | H | 1/2$H_2O$/mp. 154.3° C. |
| 1.145 | H | H | 2-$CH_3$ | 2-$C_2H_5$ | H | H | mp. 199.7° C. |
| 1.146 | H | H | H | H | 8-Cl | H | mp. 219.3° C. |
| 1.147 | H | $CH_3$ | H | H | 6-CN | H | $HNO_3$ mp. 169.6° C. |
| 1.148 | H | $CH_3$ | | 2-$(CH_2)_4$—2 | 6-CN | H | $HNO_3$ mp. 175.0° C. |
| 1.149 | H | $CH_3$ | H | H | 6-Cl | H | $HNO_3$ mp. 172.3° C. |
| 1.150 | H | H | H | H | 6-Cl | H | mp. 215.1° C. |
| 1.151 | SH | $CH_3OCH_2$ | 2-$CH_3$ | 2-$CH_3$ | H | H | |
| 1.152 | H | $CH_3OCH_2$ | 2-$CH_3$ | 2-$CH_3$ | H | H | |
| 1.153 | SH | benzyl | 2-$CH_3$ | 2-$CH_3$ | H | H | |
| 1.154 | H | benzyl | 2-$CH_3$ | 2-$CH_3$ | H | H | |
| 1.155 | SH | $CH_3$ | 2-$CH_2$—CH=$CH_2$ | H | H | H | |
| 1.156 | H | $CH_3$ | 2-$CH_2$—CH=$CH_2$ | H | H | H | |
| 1.157 | H | H | 2-$CH_2$—CH=$CH_2$ | H | H | H | |
| 1.158 | SH | $CH_3$ | | 2-$(CH_2)_3$—2 | H | H | |
| 1.159 | H | $CH_3$ | | 2-$(CH_2)_3$—2 | H | H | |
| 1.160 | H | H | 2-$C_3H_7$—i | 2-$CH_3$ | H | H | |
| 1.161 | H | H | 2-$CH_3$ | 2-$CH_3$ | 6-$CH_3$ | H | |
| 1.162 | H | H | 2-$C_6H_5$ | H | H | H | |
| 1.163 | H | H | 2-$C_3H_7$—i | 2-$CH_3$ | 6-F | H | |
| 1.164 | H | H | 2-$C_6H_{13}$—n | 2-$CH_3$ | 6-F | H | |

TABLE 1a-continued

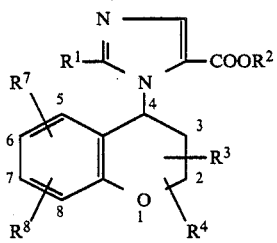

| comp. No. | R¹ | R² | R³ | R⁴ | R⁷ | R⁸ | physical data |
|---|---|---|---|---|---|---|---|
| 1.165 | H | H | 3-$CH_3$ | H | H | H | |
| 1.166 | H | H | | 2-$(CH_2)_4$—2 | 6-CN | H | |
| 1.167 | H | H | | 2-$(CH_2)_2$—2 | H | H | |
| 1.168 | H | H | | 2-$(CH_2)_3$—2 | H | H | |
| 1.169 | H | H | | 2-$(CH_2)_5$—2 | H | H | |
| 1.170 | H | H | | 2-$(CH_2)_6$—2 | H | H | |
| 1.171 | H | $CH_3$ | 2-$CH_3$ | H | H | H | HCl |
| 1.172 | H | $CH_3$ | 2-$CH_3$ | H | H | H | $CH_3SO_3H$ |
| 1.173 | H | $CH_3$ | 2-$CH_3$ | H | H | H | HBr |
| 1.174 | H | $CH_3$ | 3-$CH_3$ | H | H | H | HCl |
| 1.175 | H | $CH_3$ | 3-$CH_3$ | H | H | H | HBr |
| 1.176 | H | $CH_3$ | 3-$CH_3$ | H | H | H | $CH_3SO_3H$ |
| 1.177 | SH | $CH_3$ | 2-$CH_3$ | 3-$CH_3$ | H | H | (A + B) |
| 1.178 | H | H | 2-$CH_3$ | 3-$CH_3$ | H | H | (A + B)/mp. 245.2° C. |
| 1.179 | H | $CH_3$ | 2-$CH_3$ | 3-$CH_3$ | H | H | 2,3-cis/3,4-trans |
| 1.180 | H | $CH_3$ | 2-$CH_3$ | 3-$CH_3$ | H | H | 2,3-cis/3,4-cis |
| 1.181 | H | $CH_3$ | 2-$CH_3$ | 3-$CH_3$ | H | H | 2,3-trans/3,4-cis |
| 1.182 | H | $CH_3$ | 2-$CH_3$ | 3-$CH_3$ | H | H | 2,3-trans/3,4-trans |
| 1.183 | H | $CH_3$ | 2-$CH_3$ | 3-$CH_3$ | H | H | 2,3-cis/3,4-trans (+) |
| 1.184 | H | $CH_3$ | 2-$CH_3$ | 3-$CH_3$ | H | H | 2,3-cis/3,4-trans (−) |
| 1.185 | H | $CH_3$ | 2-$CH_3$ | 3-$CH_3$ | H | H | 2,3-cis/3,4-cis (+) |
| 1.186 | H | $CH_3$ | 2-$CH_3$ | 3-$CH_3$ | H | H | 2,3-cis/3,4-cis (−) |
| 1.187 | H | $CH_3$ | 2-$CH_3$ | 3-$CH_3$ | H | H | 2,3-trans/3,4-cis (+) |
| 1.188 | H | $CH_3$ | 2-$CH_3$ | 3-$CH_3$ | H | H | 2,3-trans/3,4-cis (−) |
| 1.189 | H | $CH_3$ | 2-$CH_3$ | 3-$CH_3$ | H | H | 2,3-trans/3,4-trans (+) |
| 1.190 | H | $CH_3$ | 2-$CH_3$ | 3-$CH_3$ | H | H | 2,3-trans/3,4-trans (−) |
| 1.191 | H | $CH_3$ | 2-$C_2H_5$ | 3-$C_2H_5$ | H | H | 2,3-cis/3,4-trans |
| 1.192 | H | $CH_3$ | 2-$C_2H_5$ | 3-$C_2H_5$ | H | H | 2,3-cis/3,4-cis |
| 1.193 | H | $CH_3$ | 2-$C_2H_5$ | 3-$C_2H_5$ | H | H | 2,3-trans/3,4-cis |
| 1.194 | H | $CH_3$ | 2-$C_2H_5$ | 3-$C_2H_5$ | H | H | 2,3-trans/3,4-trans |
| 1.195 | H | $CH_3$ | 2-$C_2H_5$ | 3-$C_2H_5$ | H | H | 2,3-cis/3,4-trans (+) |
| 1.196 | H | $CH_3$ | 2-$C_2H_5$ | 3-$C_2H_5$ | H | H | 2,3-cis/3,4-trans (−) |
| 1.197 | H | $CH_3$ | 2-$C_2H_5$ | 3-$C_2H_5$ | H | H | 2,3-cis/3,4-cis (+) |
| 1.198 | H | $CH_3$ | 2-$C_2H_5$ | 3-$C_2H_5$ | H | H | 2,3-cis/3,4-cis (−) |
| 1.199 | H | $CH_3$ | 2-$C_2H_5$ | 3-$C_2H_5$ | H | H | 2,3-trans/3,4-cis (+) |
| 1.200 | H | $CH_3$ | 2-$C_2H_5$ | 3-$C_2H_5$ | H | H | 2,3-trans/3,4-cis (−) |
| 1.201 | H | $CH_3$ | 2-$C_2H_5$ | 3-$C_2H_5$ | H | H | 2,3-trans/3,4-trans (+) |
| 1.202 | H | $CH_3$ | 2-$C_2H_5$ | 3-$C_2H_5$ | H | H | 2,3-trans/3,4-trans (−) |
| 1.203 | H | $CH_3$ | 2-$CH_3$ | 3-$C_2H_5$ | H | H | 2,3-cis/3,4-trans |
| 1.204 | H | $CH_3$ | 2-$CH_3$ | 3-$C_2H_5$ | H | H | 2,3-cis/3,4-cis |
| 1.205 | H | $CH_3$ | 2-$CH_3$ | 3-$C_2H_5$ | H | H | 2,3-trans/3,4-cis |
| 1.206 | H | $CH_3$ | 2-$CH_3$ | 3-$C_2H_5$ | H | H | 2,3-trans/3,4-trans |
| 1.207 | H | $CH_3$ | 2-$C_2H_5$ | 3-$CH_3$ | H | H | 2,3-cis/3,4-trans |
| 1.208 | H | $CH_3$ | 2-$C_2H_5$ | 3-$CH_3$ | H | H | 2,3-cis/3,4-cis |
| 1.209 | H | $CH_3$ | 2-$C_2H_5$ | 3-$CH_3$ | H | H | 2,3-trans/3,4-cis |
| 1.210 | H | $CH_3$ | 2-$C_2H_5$ | 3-$CH_3$ | H | H | 2,3-trans/3,4-trans |
| 1.211 | H | $CH_3$ | 2-$CH_3$ | 3-$C_3H_7$—n | H | H | 2,3-cis/3,4-trans |
| 1.212 | H | $CH_3$ | 2-$CH_3$ | 3-$C_3H_7$—n | H | H | 2,3-cis/3,4-cis |
| 1.213 | H | $CH_3$ | 2-$CH_3$ | 3-$C_3H_7$—n | H | H | 2,3-trans/3,4-cis |
| 1.214 | H | $CH_3$ | 2-$CH_3$ | 3-$C_3H_7$—n | H | H | 2,3-trans/3,4-trans |
| 1.215 | H | $CH_3$ | 2-$CH_3$ | 3-$C_6H_{11}$—n | H | H | 2,3-cis/3,4-trans |
| 1.216 | H | $CH_3$ | 2-$CH_3$ | 3-$C_6H_{11}$—n | H | H | 2,3-cis/3,4-cis |
| 1.217 | H | $CH_3$ | 2-$CH_3$ | 3-$C_6H_{11}$—n | H | H | 2,3-trans/3,4-cis |
| 1.218 | H | $CH_3$ | 2-$CH_3$ | 3-$C_6H_{11}$—n | H | H | 2,3-trans/3,4-trans |
| 1.219 | H | $CH_3$ | 2-$C_3H_7$—n | 3-$CH_3$ | H | H | 2,3-cis/3,4-trans |
| 1.220 | H | $CH_3$ | 2-$C_3H_7$—n | 3-$CH_3$ | H | H | 2,3-cis/3,4-cis |
| 1.221 | H | $CH_3$ | 2-$C_3H_7$—n | 3-$CH_3$ | H | H | 2,3-trans/3,4-cis |
| 1.222 | H | $CH_3$ | 2-$C_3H_7$—n | 3-$CH_3$ | H | H | 2,3-trans/3,4-trans |
| 1.223 | H | $CH_3$ | 2-$C_6H_{11}$—n | 3-$CH_3$ | H | H | 2,3-cis/3,4-trans |
| 1.224 | H | $CH_3$ | 2-$C_6H_{11}$—n | 3-$CH_3$ | H | H | 2,3-cis/3,4-cis |
| 1.225 | H | $CH_3$ | 2-$C_6H_{11}$—n | 3-$CH_3$ | H | H | 2,3-trans/3,4-cis |
| 1.226 | H | $CH_3$ | 2-$C_6H_{11}$—n | 3-$CH_3$ | H | H | 2,3-trans/3,4-trans |
| 1.227 | H | $CH_3$ | 2-$CH_3$ | H | H | H | trans (+) |
| 1.228 | H | $CH_3$ | 2-$CH_3$ | H | H | H | trans (−) |
| 1.229 | H | $CH_3$ | 2-$CH_3$ | H | H | H | cis (+) |
| 1.230 | H | $CH_3$ | 2-$CH_3$ | H | H | H | cis (−) |
| 1.231 | H | $CH_3$ | 2-$C_2H_5$ | H | H | H | cis (+) |
| 1.232 | H | $CH_3$ | 2-$C_2H_5$ | H | H | H | cis (−) |
| 1.233 | H | $CH_3$ | 2-$C_2H_5$ | H | H | H | trans (+) |

TABLE 1a-continued

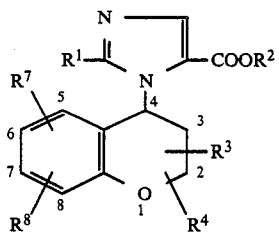

| comp. No. | R¹ | R² | R³ | R⁴ | R⁷ | R⁸ | physical data |
|---|---|---|---|---|---|---|---|
| 1.234 | H | CH₃ | 2-C₂H₅ | H | H | H | trans (−) |
| 1.235 | H | CH₃ | 2-CH₃ | H | 6-F | H | cis |
| 1.236 | H | CH₃ | 2-CH₃ | H | 6-F | H | trans |
| 1.237 | H | CH₃ | 3-CH₃ | 3-C₃H₇—i | 6-F | H | .HNO₃ |
| 1.238 | H | H | H | H | H | H | |

TABLE 1b

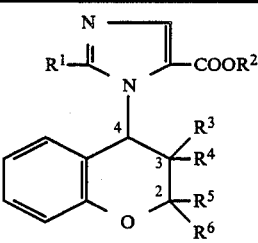

| comp. No. | R¹ | R² | R³ | R⁴ | R⁵ | R⁶ | physical data |
|---|---|---|---|---|---|---|---|
| 1.239 | SH | CH₃ | CH₃ | CH₃ | CH₃ | H | |
| 1.240 | H | CH₃ | CH₃ | CH₃ | CH₃ | H | |
| 1.241 | SH | CH₃ | CH₃ | CH₃ | CH₃ | CH₃ | |
| 1.242 | H | CH₃ | CH₃ | CH₃ | CH₃ | CH₃ | |
| 1.243 | SH | CH₃ | CH₃ | H | CH₃ | CH₃ | |
| 1.244 | H | CH₃ | CH₃ | H | CH₃ | CH₃ | |
| 1.245 | SH | CH₃ | CH₂F | CH₃ | H | H | |
| 1.246 | H | CH₃ | CH₂F | CH₃ | H | H | |
| 1.247 | H | CH₃ | CH₃ | CH₃ | C₂H₅ | H | |
| 1.248 | H | CH₃ | CH₃ | CH₃ | C₂H₅ | H | 2,4-cis |
| 1.249 | H | CH₃ | CH₃ | CH₃ | C₂H₅ | H | 2,4-trans |
| 1.250 | H | CH₃ | CH₃ | CH₃ | CH₃ | H | 2,4-cis |
| 1.251 | H | CH₃ | CH₃ | CH₃ | CH₃ | H | 2,4-trans |

TABLE 1c

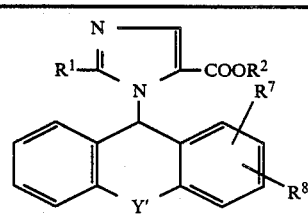

| comp. No. | R¹ | R² | Y' | R⁷ | R⁸ | physical data |
|---|---|---|---|---|---|---|
| 1.252 | SH | CH₃ | O | H | H | |
| 1.253 | H | CH₃ | O | H | H | m.p. 186.3° C. |
| 1.254 | SH | CH₃ | S | H | H | |
| 1.255 | H | CH₃ | S | H | H | |
| 1.256 | SH | CH₃ | N(CH₃) | H | H | |
| 1.257 | H | CH₃ | N(CH₃) | H | H | |
| 1.258 | SH | CH₃ | CH₂O | H | H | |
| 1.259 | H | CH₃ | CH₂O | H | H | |
| 1.260 | SH | CH₃ | CH₂S | H | H | |
| 1.261 | H | CH₃ | CH₂S | H | H | |
| 1.262 | SH | CH₃ | —CH=N— | H | H | |
| 1.263 | H | CH₃ | —CH=N— | H | H | |

TABLE 2

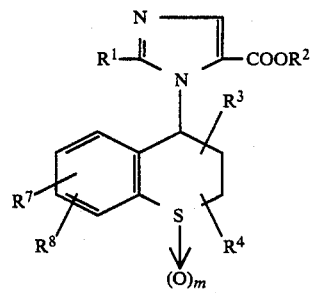

| comp. No. | R¹ | R² | m | R³ | R⁴ | R⁷ | R⁸ | physical data |
|---|---|---|---|---|---|---|---|---|
| 2.01 | H | CH₃ | 0 | H | H | H | H | |
| 2.02 | SH | CH₃ | 0 | H | H | H | H | mp. 163.3° C. |
| 2.03 | H | CH₃ | 0 | 3-CH₃ | 3-CH₃ | H | H | |
| 2.04 | SH | CH₃ | 0 | 3-CH₃ | 3-CH₃ | H | H | |
| 2.05 | H | C₂H₅ | 0 | H | H | H | H | |
| 2.06 | SH | C₂H₅ | 0 | H | H | H | H | |
| 2.07 | H | CH₃ | 0 | H | H | 6-Cl | H | |
| 2.08 | SH | CH₃ | 0 | H | H | 6-Cl | H | |
| 2.09 | H | CH₃ | 0 | 2-(CH₂)₄—2 | | 6-Cl | 8-Cl | |
| 2.10 | SH | CH₃ | 0 | 2-(CH₂)₄—2 | | 6-Cl | 8-Cl | |
| 2.11 | H | C₂H₅ | 0 | 2-(CH₂)₅—2 | | H | H | |

TABLE 2-continued

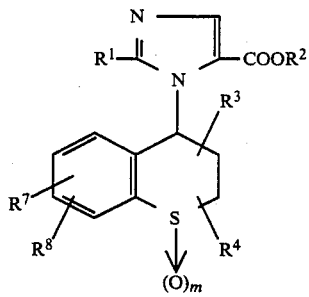

| comp. No. | R$^1$ | R$^2$ | m | R$^3$ | R$^4$ | R$^7$ | R$^8$ | physical data |
|---|---|---|---|---|---|---|---|---|
| 2.12 | SH | C$_2$H$_5$ | 0 | 2-(CH$_2$)$_5$—2 | | H | H | |
| 2.13 | H | CH$_3$ | 0 | H | H | 5-CH$_3$ | 7-CH$_3$ | |
| 2.14 | SH | CH$_3$ | 0 | H | H | 5-CH$_3$ | 7-CH$_3$ | |
| 2.15 | H | CH$_3$ | 1 | H | H | H | H | |
| 2.16 | SH | CH$_3$ | 1 | H | H | H | H | |
| 2.17 | H | CH$_3$ | 1 | 3-CH$_3$ | 3-CH$_3$ | H | H | |
| 2.18 | SH | CH$_3$ | 1 | 3-CH$_3$ | 3-CH$_3$ | H | H | |
| 2.19 | H | C$_2$H$_5$ | 1 | H | H | H | H | |
| 2.20 | SH | C$_2$H$_5$ | 1 | H | H | H | H | |
| 2.21 | H | CH$_3$ | 1 | H | H | 6-Cl | H | |
| 2.22 | SH | CH$_3$ | 1 | H | H | 6-Cl | H | |
| 2.23 | H | CH$_3$ | 1 | 2-(CH$_2$)$_4$—2 | | 6-Cl | 8-Cl | |
| 2.24 | SH | CH$_3$ | 1 | 2-(CH$_2$)$_4$—2 | | 6-Cl | 8-Cl | |
| 2.25 | H | C$_2$H$_5$ | 1 | 2-(CH$_2$)$_5$—2 | | H | H | |
| 2.26 | SH | C$_2$H$_5$ | 1 | 2-(CH$_2$)$_5$—2 | | H | H | |
| 2.27 | H | CH$_3$ | 1 | H | H | 5-CH$_3$ | 7-CH$_3$ | |
| 2.28 | SH | CH$_3$ | 1 | H | H | 5-CH$_3$ | 7-CH$_3$ | |
| 2.29 | H | CH$_3$ | 2 | H | H | H | H | |
| 2.30 | SH | CH$_3$ | 2 | H | H | H | H | |
| 2.31 | H | CH$_3$ | 2 | 3-CH$_3$ | 3-CH$_3$ | H | H | |
| 2.32 | SH | CH$_3$ | 2 | 3-CH$_3$ | 3-CH$_3$ | H | H | |
| 2.33 | H | C$_2$H$_5$ | 2 | H | H | H | H | |
| 2.34 | SH | C$_2$H$_5$ | 2 | H | H | H | H | |
| 2.35 | H | CH$_3$ | 2 | H | H | 6-Cl | H | |
| 2.36 | SH | CH$_3$ | 2 | H | H | 6-Cl | H | |
| 2.37 | H | CH$_3$ | 2 | 2-(CH$_2$)$_4$—2 | | 6-Cl | 8-Cl | |
| 2.38 | SH | CH$_3$ | 2 | 2-(CH$_2$)$_4$—2 | | 6-Cl | 8-Cl | |
| 2.39 | H | C$_2$H$_5$ | 2 | 2-(CH$_2$)$_5$—2 | | H | H | |
| 2.40 | SH | C$_2$H$_5$ | 2 | 2-(CH$_2$)$_5$—2 | | H | H | |
| 2.41 | H | CH$_3$ | 2 | H | H | 5-CH$_3$ | 7-CH$_3$ | |
| 2.42 | SH | CH$_3$ | 2 | H | H | 5-CH$_3$ | 7-CH$_3$ | |
| 2.43 | H | CH$_3$ | 0 | 2-CH$_3$ | H | H | H | |
| 2.44 | H | CH$_3$ | 0 | 2-CH$_3$ | H | H | H | cis |
| 2.45 | H | CH$_3$ | 0 | 2-CH$_3$ | H | H | H | trans |
| 2.46 | H | CH$_3$ | 0 | 2-CH$_3$ | H | H | H | cis (+) |
| 2.47 | H | CH$_3$ | 0 | 2-CH$_3$ | H | H | H | cis (−) |
| 2.48 | H | CH$_3$ | 0 | 2-CH$_3$ | H | H | H | trans (+) |
| 2.49 | H | CH$_3$ | 0 | 2-CH$_3$ | H | H | H | trans (−) |
| 2.50 | H | CH$_3$ | 0 | 2-CH$_3$ | 3-CH$_3$ | H | H | |
| 2.51 | H | CH$_3$ | 0 | 2-CH$_3$ | 3-CH$_3$ | H | H | 2,3-cis/3,4-trans |
| 2.52 | H | CH$_3$ | 0 | 2-CH$_3$ | 3-CH$_3$ | H | H | 2,3-cis/3,4-cis |
| 2.53 | H | CH$_3$ | 0 | 2-CH$_3$ | 3-CH$_3$ | H | H | 2,3-trans/3,4-cis |
| 2.54 | H | CH$_3$ | 0 | 2-CH$_3$ | 3-CH$_3$ | H | H | 2,3-trans/3,4-trans |
| 2.55 | H | CH$_3$ | 0 | 2-CH$_3$ | 3-CH$_3$ | H | H | 2,3-cis/3,4-trans (+) |
| 2.56 | H | CH$_3$ | 0 | 2-CH$_3$ | 3-CH$_3$ | H | H | 2,3-cis/3,4-trans (−) |
| 2.57 | H | CH$_3$ | 0 | 2-CH$_3$ | 3-CH$_3$ | H | H | 2,3-cis/3,4-cis (+) |
| 2.58 | H | CH$_3$ | 0 | 2-CH$_3$ | 3-CH$_3$ | H | H | 2,3-cis/3,4-cis (−) |
| 2.59 | H | CH$_3$ | 0 | 2-CH$_3$ | 3-CH$_3$ | H | H | 2,3-trans/3,4-cis (+) |
| 2.60 | H | CH$_3$ | 0 | 2-CH$_3$ | 3-CH$_3$ | H | H | 2,3-trans/3,4-cis (−) |
| 2.61 | H | CH$_3$ | 0 | 2-CH$_3$ | 3-CH$_3$ | H | H | 2,3-trans/3,4-trans (+) |
| 2.62 | H | CH$_3$ | 0 | 2-CH$_3$ | 3-CH$_3$ | H | H | 2,3-trans/3,4-trans (−) |
| 2.63 | H | CH$_3$ | 1 | 2-CH$_3$ | H | H | H | |
| 2.64 | H | CH$_3$ | 2 | 2-CH$_3$ | H | H | H | |
| 2.65 | H | CH$_3$ | 0 | 2-C$_2$H$_5$ | H | H | H | |
| 2.66 | H | CH$_3$ | 0 | 2-C$_2$H$_5$ | H | H | H | cis |
| 2.67 | H | CH$_3$ | 0 | 2-C$_2$H$_5$ | H | H | H | trans |

TABLE 3

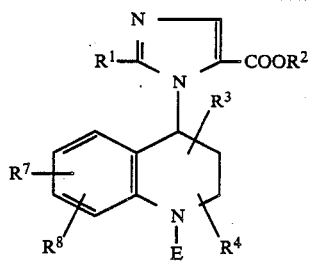

| comp. No. | R¹ | R² | R³ | R⁴ | R⁷ | R⁸ | E | physical data |
|---|---|---|---|---|---|---|---|---|
| 3.01 | H | CH$_3$ | H | H | H | H | CH$_3$ | |
| 3.02 | SH | CH$_3$ | H | H | H | H | CH$_3$ | |
| 3.03 | H | CH$_3$ | H | H | H | H | C$_2$H$_5$ | |
| 3.04 | SH | CH$_3$ | H | H | H | H | C$_2$H$_5$ | |
| 3.05 | H | C$_2$H$_5$ | H | H | H | H | COCH$_3$ | |
| 3.06 | SH | C$_2$H$_5$ | H | H | H | H | COCH$_3$ | |
| 3.07 | H | C$_2$H$_5$ | 3-CH$_3$ | 3-CH$_3$ | H | H | CH$_3$ | |
| 3.08 | SH | C$_2$H$_5$ | 3-CH$_3$ | 3-CH$_3$ | H | H | CH$_3$ | |
| 3.09 | H | CH$_3$ | 3-CH$_3$ | 4-CH$_3$ | 5-CH$_3$ | 7-CH$_3$ | H | |
| 3.10 | SH | CH$_3$ | 3-CH$_3$ | 4-CH$_3$ | 5-CH$_3$ | 7-CH$_3$ | H | |
| 3.11 | H | CH$_3$ | H | H | 6-Cl | 8-Cl | H | |
| 3.12 | SH | CH$_3$ | H | H | 6-Cl | 8-Cl | H | |
| 3.13 | H | CH$_3$ | 3-CH$_3$ | 3-CH$_3$ | H | H | CH$_3$ | |
| 3.14 | SH | CH$_3$ | 3-CH$_3$ | 3-CH$_3$ | H | H | CH$_3$ | |
| 3.15 | SH | CH$_3$ | H | H | H | H | SO$_2$—C$_6$H$_4$—CH$_3$ | mp. 211.5° C. |
| 3.16 | H | CH$_3$ | H | H | H | H | SO$_2$—C$_6$H$_4$—CH$_3$ | mp. 71.2° C. |
| 3.17 | H | CH$_3$ | H | H | H | H | SO$_2$—C$_6$H$_4$—CH$_3$ | HNO$_3$/mp. 142.3° C. |
| 3.18 | H | CH$_3$ | H | H | H | H | COCH$_3$ | mp. 153.8° C. |
| 3.19 | SH | CH$_3$ | H | H | H | H | COCH$_3$ | mp. 183.5° C. |

TABLE 4

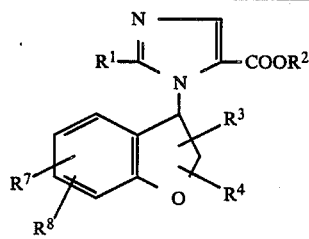

| comp. No. | R¹ | R² | R³ | R⁴ | R⁷ | R⁸ | physical data |
|---|---|---|---|---|---|---|---|
| 4.01 | H | CH$_3$ | H | H | H | H | mp. 87.5–89° C. |
| 4.02 | SH | CH$_3$ | H | H | H | H | mp. 194–195° C. |
| 4.03 | H | C$_2$H$_5$ | 2-CH$_3$ | 2-CH$_3$ | H | H | |
| 4.04 | SH | C$_2$H$_5$ | 2-CH$_3$ | 2-CH$_3$ | H | H | |
| 4.05 | H | CH$_3$ | 2-CH$_3$ | 2-CH$_3$ | H | H | HNO$_3$/mp. 166.1° C. |
| 4.06 | SH | CH$_3$ | 2-CH$_3$ | 2-CH$_3$ | H | H | |
| 4.07 | H | C$_3$H$_7$—i | H | H | 5-Cl | 7-Cl | |
| 4.08 | SH | C$_3$H$_7$—i | H | H | 5-Cl | 7-Cl | |
| 4.09 | H | CH$_3$ | H | H | 4-CH$_3$ | 6-CH$_3$ | |
| 4.10 | SH | CH$_3$ | H | H | 4-CH$_3$ | 6-CH$_3$ | |
| 4.11 | H | CH$_3$ | 2-CH$_3$ | H | H | H | trans |
| 4.12 | SH | CH$_3$ | 2-CH$_3$ | H | H | H | trans |
| 4.13 | H | CH$_3$ | 2-CH$_3$ | H | H | H | cis |
| 4.14 | SH | CH$_3$ | 2-CH$_3$ | H | H | H | cis |
| 4.15 | H | CH$_3$ | 2-C$_2$H$_5$ | H | H | H | |
| 4.16 | SH | CH$_3$ | 2-C$_2$H$_5$ | H | H | H | |
| 4.17 | H | CH$_3$ | 2-C$_3$H$_7$—i | H | H | H | |
| 4.18 | SH | CH$_3$ | 2-C$_3$H$_7$—i | H | H | H | |
| 4.19 | H | CH$_3$ | 2-C$_4$H$_9$—n | H | H | H | |
| 4.20 | SH | CH$_3$ | 2-C$_4$H$_9$—n | H | H | H | |
| 4.21 | H | CH$_3$ | 2-C$_5$H$_{11}$—n | H | H | H | |
| 4.22 | SH | CH$_3$ | 2-C$_5$H$_{11}$—n | H | H | H | |
| 4.23 | H | CH$_3$ | 2-C$_6$H$_{13}$—n | H | H | H | |
| 4.24 | SH | CH$_3$ | 2-C$_6$H$_{13}$—n | H | H | H | |
| 4.25 | H | H | H | H | H | H | |
| 4.26 | H | H | 2-CH$_3$ | 2-CH$_3$ | H | H | |
| 4.27 | H | H | H | H | 5-Cl | 7-Cl | |
| 4.28 | H | H | H | H | 4-CH$_3$ | 6-CH$_3$ | |
| 4.29 | H | H | 2-CH$_3$ | H | H | H | |
| 4.30 | H | H | 2-C$_2$H$_5$ | H | H | H | |
| 4.31 | H | H | 2-C$_3$H$_7$—i | H | H | H | |

TABLE 4-continued

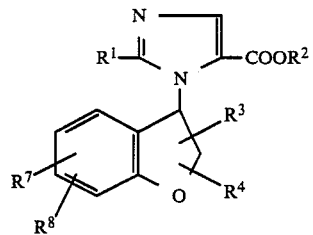

| comp. No. | $R^1$ | $R^2$ | $R^3$ | $R^4$ | $R^7$ | $R^8$ | physical data |
|---|---|---|---|---|---|---|---|
| 4.32 | H | H | 2-$C_6H_{13}$—n | H | H | H | |
| 4.33 | SH | $CH_3$ | 2-$(CH_2)_2$—2 | | H | H | |
| 4.34 | H | $CH_3$ | 2-$(CH_2)_2$—2 | | H | H | |
| 4.35 | H | H | 2-$(CH_2)_2$—2 | | H | H | |
| 4.36 | SH | $CH_3$ | 2-$(CH_2)_3$—2 | | H | H | |
| 4.37 | H | $CH_3$ | 2-$(CH_2)_3$—2 | | H | H | |
| 4.38 | H | H | 2-$(CH_2)_3$—2 | | H | H | |
| 4.39 | SH | $CH_3$ | 2-$(CH_2)_4$—2 | | H | H | |
| 4.40 | H | $CH_3$ | 2-$(CH_2)_4$—2 | | H | H | |
| 4.41 | H | H | 2-$(CH_2)_4$—2 | | H | H | |
| 4.42 | H | $CH_3$ | 2-$CH_3$ | 2-$CH_3$ | H | H | (+) |
| 4.43 | H | $CH_3$ | 2-$CH_3$ | 2-$CH_3$ | H | H | (−) |
| 4.44 | H | $CH_3$ | 2-$C_2H_5$ | 2-$C_2H_5$ | H | H | (+) |
| 4.45 | H | $CH_3$ | 2-$C_2H_5$ | 2-$C_2H_5$ | H | H | (−) |
| 4.46 | H | $CH_3$ | 2-$CH_3$ | 2-$C_2H_5$ | H | H | |

TABLE 5

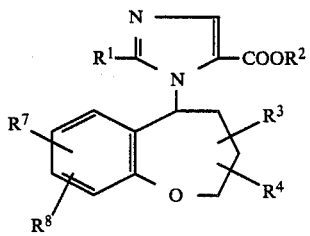

| comp. No. | $R^1$ | $R^2$ | $R^3$ | $R^4$ | $R^7$ | $R^8$ | physical data |
|---|---|---|---|---|---|---|---|
| 5.01 | H | $CH_3$ | 4-$CH_3$ | 4-$CH_3$ | H | H | |
| 5.02 | SH | $CH_3$ | 4-$CH_3$ | 4-$CH_3$ | H | H | |
| 5.03 | H | $CH_3$ | H | H | H | H | mp. 131–132° C. |
| 5.04 | SH | $CH_3$ | H | H | H | H | mp. 209° C. (dec.) |
| 5.05 | H | $C_2H_5$ | H | H | H | H | |
| 5.06 | SH | $C_2H_5$ | H | H | H | H | |
| 5.07 | H | $CH_3$ | H | H | 6-$CH_3$ | H | |
| 5.08 | SH | $CH_3$ | H | H | 7-Cl | H | |
| 5.09 | H | $C_2H_5$ | 4-$CH_3$ | 4-$CH_3$ | H | H | |
| 5.10 | SH | $C_2H_5$ | 4-$CH_3$ | 4-$CH_3$ | H | H | |
| 5.11 | H | $CH_3$ | 2-$(CH_2)_4$—2 | | H | H | |
| 5.12 | SH | $CH_3$ | 2-$(CH_2)_4$—2 | | H | H | |
| 5.13 | H | $CH_3$ | H | H | 7-$CH_3$ | 9-$CH_3$ | |
| 5.14 | H | $CH_3$ | H | H | 7-Cl | 9-Cl | |
| 5.15 | H | $CH_3$ | H | H | H | H | .$HNO_3$/mp. 163.5° C. (dec.) |
| 5.16 | H | H | H | H | H | H | mp. 202° C. (dec.) |
| 5.17 | SH | $CH_3$ | 2-$CH_3$ | H | H | H | |
| 5.18 | H | $CH_3$ | 2-$CH_3$ | H | H | H | |
| 5.19 | SH | $CH_3$ | 2-$CH_3$ | 2-$CH_3$ | H | H | |
| 5.20 | H | $CH_3$ | 2-$CH_3$ | 2-$CH_3$ | H | H | |
| 5.21 | SH | $CH_3$ | 3-$CH_3$ | H | H | H | |
| 5.22 | H | $CH_3$ | 3-$CH_3$ | H | H | H | |
| 5.23 | SH | $CH_3$ | 3-$CH_3$ | 3-$CH_3$ | H | H | |
| 5.24 | H | $CH_3$ | 3-$CH_3$ | 3-$CH_3$ | H | H | |

TABLE 6

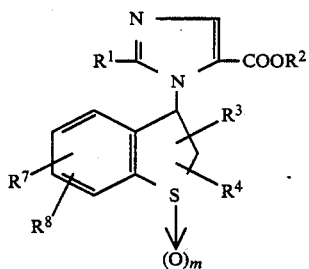

| comp. No. | $R^1$ | $R^2$ | m | $R^3$ | $R^4$ | $R^7$ | $R^8$ | physical data |
|---|---|---|---|---|---|---|---|---|
| 6.01 | H | $CH_3$ | 0 | H | H | H | H | |
| 6.02 | SH | $CH_3$ | 0 | H | H | H | H | |
| 6.03 | H | $CH_3$ | 0 | H | H | 5-Cl | 7-Cl | |
| 6.04 | SH | $CH_3$ | 0 | H | H | 5-Cl | 7-Cl | |
| 6.05 | H | $C_2H_5$ | 0 | H | H | 5-F | H | |
| 6.06 | SH | $C_2H_5$ | 0 | H | H | 5-F | H | |
| 6.07 | H | $CH_3$ | 0 | 2-$CH_3$ | 2-$CH_3$ | H | H | |
| 6.08 | SH | $CH_3$ | 0 | 2-$CH_3$ | 2-$CH_3$ | H | H | |
| 6.09 | H | $CH_3$ | 0 | 2-$CH_3$ | 2-$CH_3$ | 5-$CH_3$ | 7-$CH_3$ | |
| 6.10 | SH | $CH_3$ | 0 | 2-$CH_3$ | 2-$CH_3$ | 5-$CH_3$ | 7-$CH_3$ | |
| 6.11 | H | $C_2H_5$ | 0 | 2-$(CH_2)_4$—2 | | H | H | |
| 6.12 | SH | $C_2H_5$ | 0 | 2-$(CH_2)_4$—2 | | H | H | |
| 6.13 | H | $CH_3$ | 0 | 2-$(CH_2)_2$—2 | | H | H | |
| 6.14 | SH | $CH_3$ | 0 | 2-$(CH_2)_2$—2 | | H | H | |
| 6.15 | H | $CH_3$ | 1 | H | H | H | H | |
| 6.16 | SH | $CH_3$ | 1 | H | H | H | H | |
| 6.17 | H | $CH_3$ | 1 | 2-$CH_3$ | 2-$CH_3$ | H | H | |
| 6.18 | SH | $CH_3$ | 1 | 2-$CH_3$ | 2-$CH_3$ | H | H | |
| 6.19 | H | $C_2H_5$ | 1 | 2-$(CH_2)_4$—2 | | H | H | |
| 6.20 | SH | $C_2H_5$ | 1 | 2-$(CH_2)_4$—2 | | H | H | |
| 6.21 | H | $CH_3$ | 1 | 2-$(CH_2)_2$—2 | | H | H | |
| 6.22 | SH | $CH_3$ | 1 | 2-$(CH_2)_2$—2 | | H | H | |
| 6.23 | H | $CH_3$ | 2 | H | H | H | H | |
| 6.24 | SH | $CH_3$ | 2 | H | H | H | H | |
| 6.25 | H | $CH_3$ | 2 | 2-$CH_3$ | 2-$CH_3$ | H | H | |
| 6.26 | SH | $CH_3$ | 2 | 2-$CH_3$ | 2-$CH_3$ | H | H | |
| 6.27 | H | $C_2H_5$ | 2 | 2-$(CH_2)_4$—2 | | H | H | |
| 6.28 | SH | $C_2H_5$ | 2 | 2-$(CH_2)_4$—2 | | H | H | |
| 6.29 | H | $CH_3$ | 2 | 2-$(CH_2)_2$—2 | | H | H | |
| 6.30 | SH | $CH_3$ | 2 | 2-$(CH_2)_2$—2 | | H | H | |
| 6.31 | H | $CH_3$ | 0 | 2-$CH_3$ | 2-$CH_3$ | H | H | (+) |
| 6.32 | H | $CH_3$ | 0 | 2-$CH_3$ | 2-$CH_3$ | H | H | (−) |
| 6.33 | H | $CH_3$ | 0 | 2-$C_2H_5$ | 2-$C_2H_5$ | H | H | |
| 6.34 | H | $CH_3$ | 0 | 2-$C_2H_5$ | 2-$C_2H_5$ | H | H | (+) |
| 6.35 | H | $CH_3$ | 0 | 2-$C_2H_5$ | 2-$C_2H_5$ | H | H | (−) |
| 6.36 | H | $CH_3$ | 0 | 2-$CH_3$ | 2-$C_2H_5$ | H | H | |
| 6.37 | H | $CH_3$ | 0 | 2-$C_2H_5$ | 2-$CH_3$ | H | H | |
| 6.38 | H | $CH_3$ | 0 | 2-$CH_3$ | H | H | H | |
| 6.39 | H | $CH_3$ | 0 | 2-$CH_3$ | H | H | H | cis |
| 6.40 | H | $CH_3$ | 0 | 2-$CH_3$ | H | H | H | trans |
| 6.41 | H | $CH_3$ | 0 | 2-$C_2H_5$ | H | H | H | |
| 6.42 | H | $CH_3$ | 0 | 2-$C_2H_5$ | H | H | H | cis |
| 6.43 | H | $CH_3$ | 0 | 2-$C_2H_5$ | H | H | H | trans |
| 6.44 | H | $CH_3$ | 1 | 2-$CH_3$ | H | H | H | |
| 6.45 | H | $CH_3$ | 1 | 2-$C_2H_5$ | H | H | H | |
| 6.46 | H | $CH_3$ | 1 | 2-$C_2H_5$ | 2-$C_2H_5$ | H | H | |
| 6.47 | H | $CH_3$ | 2 | 2-$CH_3$ | H | H | H | |
| 6.48 | H | $CH_3$ | 2 | 2-$C_2H_5$ | H | H | H | |
| 6.49 | H | $CH_3$ | 2 | 2-$C_2H_5$ | 2-$C_2H_5$ | H | H | |
| 6.50 | H | $CH_3$ | 2 | 2-$CH_3$ | H | H | H | cis |
| 6.51 | H | $CH_3$ | 2 | 2-$CH_3$ | H | H | H | trans |
| 6.52 | H | $CH_3$ | 2 | 2-$C_2H_5$ | H | H | H | cis |
| 6.53 | H | $CH_3$ | 2 | 2-$C_2H_5$ | H | H | H | trans |

TABLE 7a

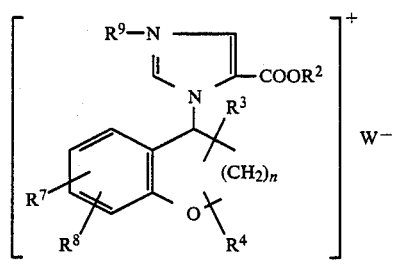

| comp. No. | n | R² | R³ | R⁴ | R⁷ | R⁸ | R⁹ | W | physical data |
|---|---|---|---|---|---|---|---|---|---|
| 7.01 | 2 | CH₃ | 2-CH₃ | H | H | H | CH₃ | I | |
| 7.02 | 2 | CH₃ | 2-CH₃ | H | H | H | CH₃ | OSO₂CH₃ | |
| 7.03 | 2 | CH₃ | 2-CH₃ | H | H | H | CH₃ | OSO₂OCH₃ | |
| 7.04 | 2 | CH₃ | 2-CH₃ | H | H | H | CH₃ | I | trans |
| 7.05 | 2 | CH₃ | 2-CH₃ | H | H | H | CH₃ | I | cis |
| 7.06 | 2 | CH₃ | 2-CH₃ | H | H | H | C₂H₅ | I | |
| 7.07 | 2 | CH₃ | 2-CH₃ | H | H | H | C₃H₇n | Br | |
| 7.08 | 2 | CH₃ | 2-CH₃ | H | H | H | C₄H₉n | Br | |
| 7.09 | 2 | CH₃ | 2-CH₃ | H | H | H | CH₂—C₆H₅ | Br | |
| 7.10 | 2 | CH₃ | 2-CH₃ | H | H | H | CH₂—C₆H₅ | Cl | |
| 7.11 | 2 | CH₃ | 2-CH₃ | 2-CH₃ | 6-CH₃ | H | CH₂C₆H₅ | Br | |
| 7.12 | 2 | CH₃ | 2-CH₃ | H | H | H | CH₂CO—4-ClC₆H₄ | Br | |
| 7.13 | 2 | CH₃ | 2-CH₃ | H | H | H | CH₂CO—C₆H₅ | Br | |
| 7.14 | 2 | CH₃ | 2-CH₃ | H | H | H | CH₂CO—2,4-(Cl)₂—C₆H₃ | Cl | |
| 7.15 | 2 | CH₃ | 2-CH₃ | H | H | H | CH₂—CH=CH₂ | Br | |
| 7.16 | 2 | CH₃ | 2-CH₃ | H | H | H | CH₂—C≡CH₂ | Br | |
| 7.17 | 2 | CH₃ | H | H | H | H | CH₃ | I | |
| 7.18 | 2 | CH₃ | 2-CH₃ | 2-CH₃ | H | H | CH₃ | I | |
| 7.19 | 2 | CH₃ | H | H | 6-Br | H | CH₃ | I | |
| 7.20 | 2 | CH₃ | 2-(CH₂)₅—2 | | H | H | CH₃ | I | |
| 7.21 | 2 | CH₃ | 2-(CH₂)₄—2 | | H | H | CH₃ | I | |
| 7.22 | 2 | C₂H₅ | 2-CH₃ | H | H | H | CH₃ | I | |
| 7.23 | 2 | C₂H₅ | 2-CH₃ | H | H | H | CH₃ | I | trans |
| 7.24 | 2 | C₂H₅ | 2-CH₃ | H | H | H | CH₃ | I | cis |
| 7.25 | 1 | CH₃ | 2-CH₃ | H | H | H | CH₃ | I | |
| 7.26 | 1 | CH₃ | 2-CH₃ | H | H | H | CH₃ | I | trans |
| 7.27 | 1 | CH₃ | 2-CH₃ | H | H | H | CH₃ | I | cis |
| 7.28 | 1 | C₂H₅ | 2-CH₃ | H | H | H | CH₃ | I | |

TABLE 7b

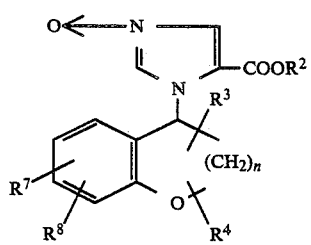

| comp. No. | n | R² | R³ | R⁴ | R⁷ | R⁸ | physical data |
|---|---|---|---|---|---|---|---|
| 7.100 | 2 | CH₃ | 2-CH₃ | H | H | H | |
| 7.101 | 2 | CH₃ | 2-CH₃ | H | H | H | trans |
| 7.102 | 2 | CH₃ | 2-CH₃ | H | H | H | cis |
| 7.103 | 2 | CH₃ | 2-CH₃ | H | H | H | |
| 7.104 | 2 | CH₃ | 2-CH₃ | H | H | H | |
| 7.105 | 2 | CH₃ | 2-CH₃ | H | H | H | |
| 7.106 | 2 | CH₃ | 2-CH₃ | H | H | H | |
| 7.107 | 2 | CH₃ | 2-CH₃ | H | H | H | |
| 7.108 | 2 | CH₃ | 2-CH₃ | H | H | H | |
| 7.109 | 2 | CH₃ | 2-CH₃ | H | H | H | |
| 7.110 | 2 | CH₃ | 2-CH₃ | H | H | H | |

TABLE 7b-continued

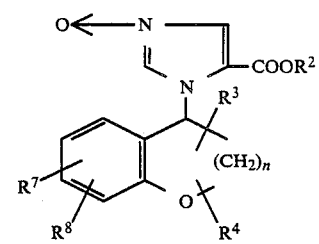

| comp. No. | n | R² | R³ | R⁴ | R⁷ | R⁸ | physical data |
|---|---|---|---|---|---|---|---|
| 7.111 | 2 | CH₃ | H | H | H | H | |
| 7.112 | 2 | CH₃ | 2-CH₃ | 2-CH₃ | H | H | |
| 7.113 | 2 | CH₃ | H | H | 6-Br | H | |
| 7.114 | 2 | CH₃ | 2-(CH₂)₅—2 | | H | H | |
| 7.115 | 2 | CH₃ | 2-(CH₂)₄—2 | | H | H | |
| 7.116 | 2 | C₂H₅ | 2-CH₃ | H | H | H | |
| 7.117 | 1 | CH₃ | 2-CH₃ | H | H | H | |
| 7.118 | 1 | CH₃ | 2-CH₃ | H | H | H | trans |
| 7.119 | 1 | CH₃ | 2-CH₃ | H | H | H | cis |
| 7.120 | 1 | C₂H₅ | 2-CH₃ | H | H | H | |
| 7.121 | 2 | CH₃ | 2-CH₃ | 2-CH₃ | 6-CH₃ | H | |

TABLE 8

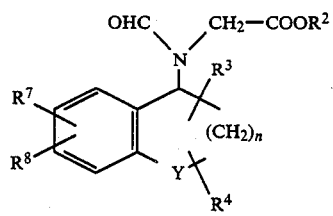

| comp. No. | n | R² | R³ | R⁴ | R⁷ | R⁸ | Y | physical data |
|---|---|---|---|---|---|---|---|---|
| 8.01 | 1 | CH₃ | H | H | H | H | —O—CH₂— | m.p. 115–118° C. |
| 8.02 | 1 | CH₃ | H | H | 6-Cl | 8-Cl | —O—CH₂— | |
| 8.03 | 1 | CH₃ | H | H | 6-F | H | —O—CH₂— | |
| 8.04 | 1 | CH₃ | 2-CH₃ | 2-CH₃ | H | H | —O—CH₂— | |
| 8.05 | 1 | CH₃ | H | H | 6-Br | H | —O—CH₂— | |
| 8.06 | 1 | CH₃ | H | H | 8-Cl | H | —O—CH₂— | m.p. 103.4° C. |
| 8.07 | 1 | CH₃ | 2-(CH₂)₄—2 | | 6-F | H | —O—CH₂— | |
| 8.08 | 1 | CH₃ | 2-(CH₂)₄—2 | | H | H | —O—CH₂— | |
| 8.09 | 1 | CH₃ | 2-(CH₂)₅—2 | | H | H | —O—CH₂— | |
| 8.10 | 1 | CH₃ | 2-C₆H₅ | H | H | H | —O—CH₂— | m.p. 87.0° C. |
| 8.11 | 1 | CH₃ | 2-C₆H₅ | 2-CH₃ | H | H | —O—CH₂— | |
| 8.12 | 1 | CH₃ | 2-C₃H₇—i | 2-CH₃ | H | H | —O—CH₂— | m.p. 109.6° C. |
| 8.13 | 1 | CH₃ | 2-CH₃ | 2-CH₃ | 6-CH₃ | H | —O—CH₂— | |
| 8.14 | 1 | CH₃ | 2-(CH₂)₄—2 | | 7-CH₃ | H | —O—CH₂— | |
| 8.15 | 1 | CH₃ | 2-(CH₂)₄—2 | | 6-OCH₃ | H | —O—CH₂— | |
| 8.16 | 1 | CH₃ | 2-CH₃ | 2-CH₃ | 7-CH₃ | H | —O—CH₂— | |
| 8.17 | 2 | CH₃ | 4-CH₃ | 4-CH₃ | H | H | —O—CH₂— | resin |
| 8.18 | 2 | CH₃ | H | H | H | H | —O—CH₂— | |
| 8.19 | 0 | CH₃ | H | H | H | H | —O—CH₂— | |
| 8.20 | 1 | CH₃ | 3-CH₃ | 3-CH₃ | H | H | —O—CH₂— | |
| 8.21 | 1 | CH₃ | 3-CH₃ | H | H | H | —O—CH₂— | |
| 8.22 | 1 | CH₃ | H | H | H | H | —S—CH₂— | |
| 8.23 | 1 | CH₃ | H | H | H | H | —N(CH₃)—CH₂— | |
| 8.24 | 1 | CH₃ | H | H | H | H | —N(C₂H₅)CH₂— | |
| 8.25 | 1 | C₂H₅ | H | H | H | H | —O—CH₂— | |
| 8.26 | 1 | C₄H₉—n | H | H | H | H | —O—CH₂— | |
| 8.27 | 1 | C₃H₇—i | H | H | H | H | —O—CH₂— | |
| 8.28 | 1 | CH₃ | 3-CH₃ | 3-CH₃ | H | H | —S—CH₂— | |
| 8.29 | 1 | C₂H₅ | H | H | H | H | —S—CH₂— | |
| 8.30 | 1 | CH₃ | 3-CH₃ | 3-CH₃ | H | H | —N(CH₃)—CH₂— | |
| 8.31 | 1 | C₂H₅ | 2-CH₃ | 2-CH₃ | 7-CH₃ | H | —O—CH₂— | |
| 8.32 | 0 | CH₃ | 2-CH₃ | 2-CH₃ | H | H | —O—CH₂— | |
| 8.33 | 1 | CH₃ | H | H | 6-Cl | H | —S—CH₂— | |
| 8.34 | 1 | CH₃ | H | H | 6-Cl | H | —O—CH₂— | |
| 8.35 | 1 | CH₃ | 2-C₆H₁₃ | 2-CH₃ | 6-F | H | —O—CH₂— | |
| 8.36 | 1 | CH₃ | 2-CH₃ | H | H | H | —O—CH₂— | m.p. 130.2° C. |
| 8.37 | 1 | CH₃ | 2-C₃H₇—i | 2-CH₃ | 6-F | H | —O—CH₂— | m.p. 115.4° C. |
| 8.38 | 1 | CH₃ | 3-benzyl | H | H | H | —O—CH₂— | |
| 8.39 | 1 | CH₃ | H | H | H | H | —SO₂—C₆H₄—CH₃ | m.p. 136.0° C. |
| 8.40 | 1 | CH₃ | 2-CH₃ | H | H | H | —O—CH₂— | cis/m.p. 131.4° C. |
| 8.41 | 1 | CH₃ | 2-CH₃ | H | H | H | —O—CH₂— | trans |
| 8.42 | 0 | CH₃ | 2-CH₃ | H | H | H | —O—CH₂— | cis |
| 8.43 | 0 | CH₃ | 2-CH₃ | H | H | H | —O—CH₂— | trans |
| 8.44 | 0 | CH₃ | 2-C₂H₅ | H | H | H | —O—CH₂— | |
| 8.45 | 0 | CH₃ | 2-C₃H₇—i | H | H | H | —O—CH₂— | |
| 8.46 | 0 | CH₃ | 2-C₄H₉—n | H | H | H | —O—CH₂— | |
| 8.47 | 0 | CH₃ | 2-C₅H₁₁—n | H | H | H | —O—CH₂— | |
| 8.48 | 0 | CH₃ | 2-C₆H₁₃—n | H | H | H | —O—CH₂— | |
| 8.49 | 0 | CH₃ | 2=CH—CH=CH—CH=3 | | H | H | —O—CH₂— | |
| 8.50 | 1 | CH₃ | 2-C₂H₅ | H | H | H | —O—CH₂— | cis |
| 8.51 | 1 | CH₃ | 2-C₂H₅ | H | H | H | —O—CH₂— | trans |

TABLE 9

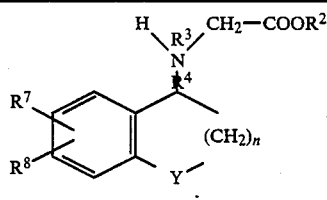

| comp. No. | n | R² | R³ | R⁴ | R⁷ | R⁸ | Y | physical data |
|---|---|---|---|---|---|---|---|---|
| 9.01 | 1 | CH₃ | H | H | H | H | —O—CH₂— | |
| 9.02 | 1 | CH₃ | H | H | 6-Cl | 8-Cl | —O—CH₂— | |
| 9.03 | 1 | CH₃ | H | H | 6-F | H | —O—CH₂— | |
| 9.04 | 1 | CH₃ | 2-CH₃ | 2-CH₃ | H | H | —O—CH₂— | |
| 9.05 | 1 | CH₃ | H | H | 6-Br | H | —O—CH₂— | |
| 9.06 | 1 | CH₃ | H | H | 8-Cl | H | —O—CH₂— | |
| 9.07 | 1 | CH₃ | 2-(CH₂)₄—2 | | 6-F | H | —O—CH₂— | |
| 9.08 | 1 | CH₃ | 2-(CH₂)₄—2 | | H | H | —O—CH₂— | |
| 9.09 | 1 | CH₃ | 2-(CH₂)₅—2 | | H | H | —O—CH₂— | |
| 9.10 | 1 | CH₃ | 2-C₆H₅ | H | H | H | —O—CH₂— | |
| 9.11 | 1 | CH₃ | 2-C₆H₅ | 2-CH₃ | H | H | —O—CH₂— | |
| 9.12 | 1 | CH₃ | 2-C₃H₇—i | 2-CH₃ | H | H | —O—CH₂— | |
| 9.13 | 1 | CH₃ | 2-CH₃ | 2-CH₃ | 6-CH₃ | H | —O—CH₂— | oil |
| 9.14 | 1 | CH₃ | 2-(CH₂)₄—2 | | 7-CH₃ | H | —O—CH₂— | oil |
| 9.15 | 1 | CH₃ | 2-(CH₂)₄—2 | | 6-OCH₃ | H | —O—CH₂— | oil |
| 9.16 | 1 | CH₃ | 2-CH₃ | 2-CH₃ | 7-CH₃ | H | —O—CH₂— | oil |
| 9.17 | 2 | CH₃ | 4-CH₃ | 4-CH₃ | H | H | —O—CH₂— | oil |
| 9.18 | 2 | CH₃ | H | H | H | H | —O—CH₂— | |
| 9.19 | 0 | CH₃ | H | H | H | H | —O—CH₂— | |
| 9.20 | 1 | CH₃ | 3-CH₃ | 3-CH₃ | H | H | —O—CH₂— | |
| 9.21 | 1 | CH₃ | 3-CH₃ | H | H | H | —O—CH₂— | |
| 9.22 | 1 | CH₃ | H | H | H | H | —S—CH₂— | |
| 9.23 | 1 | CH₃ | H | H | H | H | —N(CH₃)—CH₂— | |
| 9.24 | 1 | CH₃ | H | H | H | H | —N(C₂H₅)—CH₂— | |
| 9.25 | 1 | C₂H₅ | H | H | H | H | —O—CH₂— | |
| 9.26 | 1 | C₄H₉—n | H | H | H | H | —O—CH₂— | |
| 9.27 | 1 | C₃H₇—i | H | H | H | H | —O—CH₂— | |
| 9.28 | 1 | CH₃ | 3-CH₃ | 3-CH₃ | H | H | —S—CH₂— | |
| 9.29 | 1 | C₂H₅ | H | H | H | H | —S—CH₂— | |
| 9.30 | 1 | CH₃ | 3-CH₃ | 3-CH₃ | H | H | —N(CH₃)—CH₂— | |
| 9.31 | 1 | C₂H₅ | 2-CH₃ | 2-CH₃ | 7-CH₃ | H | —O—CH₂— | |
| 9.32 | 0 | CH₃ | 2-CH₃ | 2-CH₃ | H | H | —O—CH₂— | |
| 9.33 | 1 | CH₃ | H | H | 6-Cl | H | —S—CH₂— | |
| 9.34 | 1 | CH₃ | H | H | 6-Cl | H | —O—CH₂— | |
| 9.35 | 1 | CH₃ | 2-C₆H₁₃ | 2-CH₃ | 6-F | H | —O—CH₂— | |
| 9.36 | 1 | CH₃ | 2-CH₃ | H | H | H | —O—CH₂— | |
| 9.37 | 1 | CH₃ | 2-C₃H₇—i | 2-CH₃ | 6-F | H | —O—CH₂— | |
| 9.38 | 1 | CH₃ | 3-benzyl | H | H | H | —O—CH₂— | oil |
| 9.39 | 1 | CH₃ | H | H | H | H | SO₂-C₆H₄-CH₃ | |
| 9.40 | 1 | CH₃ | 2-CH₃ | H | H | H | —O—CH₂— | trans |
| 9.41 | 1 | CH₃ | 2-CH₃ | H | H | H | —O—CH₂— | cis |
| 9.42 | 1 | CH₃ | 2=CH—CH=CH—CH=3 | | H | H | —O—CH₂— | |
| 9.43 | 1 | CH₃ | 2-C₂H₅ | H | H | H | —O—CH₂— | |

TABLE 10

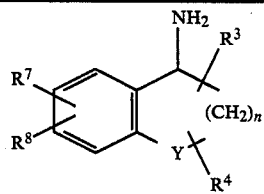

| comp. No. | n | R³ | R⁴ | R⁷ | R⁸ | Y | physical data |
|---|---|---|---|---|---|---|---|
| 10.01 | 1 | H | H | H | H | —O—CH₂— | |
| 10.02 | 1 | H | H | 6-Cl | 8-Cl | —O—CH₂— | |
| 10.03 | 1 | H | H | 6-F | H | —O—CH₂— | |
| 10.04 | 1 | 2-CH₃ | 2-CH₃ | H | H | —O—CH₂— | |
| 10.05 | 1 | H | H | 6-Br | H | —O—CH₂— | |
| 10.06 | 1 | H | H | 8-Cl | H | —O—CH₂— | |

TABLE 10-continued

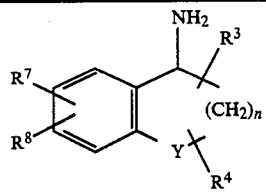

| comp. No. | n | R³ | R⁴ | R⁷ | R⁸ | Y | physical data |
|---|---|---|---|---|---|---|---|
| 10.07 | 1 | 2-(CH₂)₄—2 | | 6-F | H | —O—CH₂— | |
| 10.08 | 1 | 2-(CH₂)₄—2 | | H | H | —O—CH₂— | |
| 10.09 | 1 | 2-(CH₂)₅—2 | | H | H | —O—CH₂— | |
| 10.10 | 1 | 2-C₆H₅ | H | H | H | —O—CH₂— | |
| 10.11 | 1 | 2-C₆H₅ | 2-CH₃ | H | H | —O—CH₂— | |
| 10.12 | 1 | 2-C₃H₇—i | 2-CH₃ | H | H | —O—CH₂— | |
| 10.13 | 1 | 2-CH₃ | 2-CH₃ | 6-CH₃ | H | —O—CH₂— | oil |
| 10.14 | 1 | 2-(CH₂)₄—2 | | 7-CH₃ | H | —O—CH₂— | oil |
| 10.15 | 1 | 2-(CH₂)₄—2 | | 6-OCH₃ | H | —O—CH₂— | oil |
| 10.16 | 1 | 2-CH₃ | 2-CH₃ | 7-CH₃ | H | —O—CH₂— | oil |
| 1.017 | 2 | 4-CH₃ | 4-CH₃ | H | H | —O—CH₂— | oil |
| 10.18 | 2 | H | H | H | H | —O—CH₂— | |
| 10.19 | 0 | H | H | H | H | —O—CH₂— | |
| 10.20 | 1 | 3-CH₃ | 3-CH₃ | H | H | —O—CH₂— | |
| 10.21 | 1 | 3-CH₃ | H | H | H | —O—CH₂— | |
| 10.22 | 1 | H | H | H | H | —S—CH₂— | |
| 10.23 | 1 | H | H | H | H | —N(CH₃)—CH₂— | |
| 10.24 | 1 | H | H | H | H | —N(C₂H₅)—CH₂— | |
| 10.28 | 1 | 3-CH₃ | 3-CH₃ | H | H | —S—CH₂— | |
| 10.30 | 1 | 3-CH₃ | 3-CH₃ | H | H | —N(CH₃)—CH₂— | |
| 10.31 | 1 | 2-CH₃ | 2-CH₃ | 7-CH₃ | H | —O—CH₂— | |
| 10.32 | 0 | 2-CH₃ | 2-CH₃ | H | H | —O—CH₂— | |
| 10.33 | 1 | H | H | 6-Cl | H | —S—CH₂— | |
| 10.34 | 1 | 2-C₃H₇—i | 2-CH₃ | 6-F | H | —O—CH₂ | |
| 10.35 | 1 | 2-C₆H₁₃ | 2-CH₃ | 6-F | H | —O—CH₂— | |
| 10.36 | 1 | 2-CH₃ | H | H | H | —O—CH₂— | |
| 10.37 | 1 | 3-benzyl | H | H | H | —O—CH₂ | m.p. 252.3° C. |

(B) COMPOSITION EXAMPLES

Example 18

Composition exaples for solid compounds of formula (I) (percentages are by weight)

| (a) Wettable powders | (a) | (b) | (c) |
|---|---|---|---|
| compound of formula (I) | 20% | 50% | 0.5% |
| sodium lignosulfonate | 5% | 5% | 5% |
| sodium laurylsulfate | 3% | — | — |
| sodium diisobutylnaphthalensulfonate | — | 6% | 6% |
| octylphenol polyethylene glycol ether (7-8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient was thoroughly mixed with the adjuvants and the mixture was thoroughly groun in a suitable mill, affording wettable powders which could be diluted with water to give suspensions of the desired concentration.

| (b) Emulsifiable concentrate | (a) | (b) |
|---|---|---|
| compound of formula (I) | 10% | 1% |
| octylphenol polyethylene glycol ether (4-5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| dimethylbenzene mixture | 50% | 79% |

Emulsions of any required concentration could be obtained from this concentrate by dilution with water.

| (c) Dusts | (a) | (b) |
|---|---|---|
| compound of formula (I) | 0.1% | 1% |
| talcum | 99.9% | — |
| kaolin | — | 99% |

Usable dusts were obtained by mixing the active ingredient with the carriers, and grinding the mixture in a suitable mill.

| (d) Extruder granulate | (a) | (b) |
|---|---|---|
| compound of formula (I) | 10% | 1% |
| sodium lignosulfate | 2% | 2% |
| carboxymethylcellulose | 1% | 1% |
| kaolin | 87% | 96% |

The active ingredient was mixed and ground with the adjuvants, and the mixture was subsequently moistened with water. The mixture was extruded and dried in a stream of air.

| (e) Coated granulate | |
|---|---|
| compound of formula (I) | 3% |
| polyethylene glycol (mol. wt. 200) | 2% |
| kaolin | 94% |

The finely ground active ingredient was uniformly applied, in a mixer, to the kaolin moistened with polyethylene glycol. Non-dusty coated granulates were obtained in this manner.

| (f) Suspension concentrate | (a) | (b) |
|---|---|---|
| compound of formula (I) | 40% | 5% |
| ethylene glycol | 10% | 10% |
| nonylphenol polyethylene glycol ether (15 moles of ethylene oxide) | 6% | 1% |
| sodium lignosulfate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient was intimately mixed with the adjuvants, giving a suspension concentrate from which suspension of any desired concentration could be obtained by dilution with water.

| (g) Salt solution | |
|---|---|
| compound of formula (I) | 5% |
| isopropylamine | 1% |
| octylphenol polyethylene glycol ether (78 moles of ethylene oxide) | 3% |
| water 91 | |

Example 19

Composition examples for liquid active ingredients of formula (I)

(throughout, percentages are by weight)

| (a) Emulsifiable concentrates | (a) | (b) | (c) |
|---|---|---|---|
| compound of formula (I) | 20% | 40% | 50% |
| calcium dodecylbenzenesulfonate | 5% | 8% | 5.8% |
| castor oil polyethylene glycol ether (36 moles of ethylene oxide | 5% | — | — |
| tributylphenol polyethylene glycol ether (30 moles of ethylene oxide) | — | 12% | 4.2% |
| cyclohexanone | — | 15% | 20% |
| dimethylbenzene mixture | 70% | 25% | 20% |

Emulsions of any required concentration could be produced from such concentrate by dilution with water.

| (b) Solutions | (a) | (b) | (c) | (d) |
|---|---|---|---|---|
| compound of formula (I) | 80% | 10% | 5% | 95% |
| ethylene glycol monoethyl ether | 20% | — | — | — |
| polyethylene glycol (MG 400) | — | 70% | — | — |
| N—methyl-2-pyrrolidone | — | 20% | — | — |
| epoxidised coconut oil | — | — | 1% | 5% |
| petroleum distillate (boiling range 160–190° C.) | — | — | 94% | — |

These solutions were suitable for application in the form of microdrops.

| (c) Granulates | (a) | (b) |
|---|---|---|
| compound of formula (I) | 5% | 10% |
| kaolin | 94% | — |
| highly dispersed silicic acid | 1% | — |
| attapulgite | — | 90% |

The active ingredient was dissolved in methylene chloride, the solution was sprayed onto the carrier, and the solvent was subsequently evaporated off in vacuo.

| (d) Dusts | (a) | (b) |
|---|---|---|
| compound of formula (I) | 2% | 5% |
| highly dispersed silicic acid | 1% | 5% |
| talcum | 97% | — |
| kaolin | — | 90% |

Ready-for-use dusts were obtained by intimately mixing the carriers with the active ingredient.

(C) BIOLOGICAL EXAMPLES

Example 20

Preemergence herbicidal action

In a greenhouse, immediately after sowing the test plants in seed dishes, the surface of the soil was treated with an aqueous dispersion of the test compounds, obtained from a 25% emulsifiable concentrate or from a 25% wettable powder with test compounds, which, on account of their insufficient solubility, could not be formulates to emulsifiable concentrates. Two different concentration series were used, corresponding to 1 and 0.5 kg of test compound per hectare respectively. The seed dishes were kept in the greenhouse at 22°~25° C. and 50~70% relative humidity. The test was evaluated 3 weeks later in accordance with the following rating:

1 = plants had not germinated or were totally withered

2–3 = very strong action

4–6 = average action

7–8 = slight action

9 = no action

In this test, the tested compounds of formula (I) were most effective against a large number of weeds, whereas no or only slight damage was caused to cultivated plants such as maize at the given rates of application.

| | Results: Preemergence test | | | | | | | |
|---|---|---|---|---|---|---|---|---|
| | dosage kg a.i./ha | | | | | | | |
| | Comp. 1.01 | | Comp. 1.04 | | Comp. 1.66 | | Comp. 1.73 | |
| plant tested | 1 | 0.5 | 1 | 0.5 | 1 | 0.5 | 1 | 0.5 |
| maize | 8 | 9 | 7 | 9 | 7 | 8 | 5 | 7 |
| alopecurus myos. | 1 | 7 | 4 | 6 | 3 | 4 | 3 | 5 |
| digitaria sang. | 1 | 1 | 1 | 2 | 1 | 1 | 1 | 1 |
| echinochloa c.g. | 2 | 7 | 1 | 2 | 1 | 1 | 2 | 3 |
| sida spinosa | 5 | 9 | 2 | 3 | 2 | 2 | 2 | 2 |
| amaranthus ret. | 3 | 4 | 2 | 2 | 2 | 3 | 2 | 2 |
| chenopodium sp. | 2 | 3 | 2 | 3 | 2 | 2 | 1 | 2 |
| solanum nigrum | 1 | 1 | 1 | 1 | 1 | 1 | 2 | 2 |
| chrysanthe. leuc. | 2 | 2 | 3 | 4 | 2 | 3 | 2 | 2 |
| galium aparine | 2 | 3 | 2 | 2 | 3 | 3 | 2 | 3 |
| viola tricolor | 2 | 2 | 2 | 2 | 2 | 2 | 2 | 2 |
| veronia sp. | 3 | 3 | 1 | 1 | 1 | 1 | 1 | 2 |

Example 21

Postemergence herbicidal action (Contact herbicide)

A large number of weeds and cultivated plants were sprayed postemergence in the 4- to 6-leaf stage with an aqueous active ingredient dispersion in rates of 4 and 2 kg or 2 and 1 kg of test compound per hectare and kept at 24°~26° C. and 45~60% relative humidity. The test was evaluted at least 15 days after treatment in accordance with the same rating as employed in the preemergence test.

In this test, the compounds of formula (I) were also most effective against the tested weeds. The cultivated plants such as maize and rice were either not damaged or only damaged at higher application rates of the tested compound.

Results: Postemergence test

| plant tested | dosage kg. a.i./ha Comp. 1.66 | |
|---|---|---|
| | 2.0 | 1.0 |
| maize | 7 | 9 |
| rice, dry | 7 | 8 |
| Cyperus escul. | 3 | 3 |
| xanthium sp. | 2 | 3 |
| chenopodium sp. | 2 | 2 |
| solanum nigrum | 2 | 2 |
| ipomoena | 3 | 3 |
| veronica ssp. | 2 | 2 |

Example 22

Herbicidal action in transplanted rice crops 25 days old rice shoots of the variety "Yamabiko" were transplanted into large plastic containers. Into the same containers seeds of the weeds occuring in rice crops, namely echinochloa, scirpus, monochoria and sagittaria were sown between the rice plants. The containers were watered to such an extent, that a water layer of 2.5 cm covered the surface. After 3 days under greenhouse conditions, the dilutes aqueous dispersions of the active compounds were added to the water layer at a rate of application of 2000, 1000, 500, 250, 125 and 60 g a.i. per hectare. The containers were then kept covered with water at a temperature 25° C. and high humidity in a greenhouse for 4 weeks. The evaluation of the tests was made in accordance with the rating given in Example 20.

Results:

| Tested plant | Compound No. 1.04 in g a.i. per hectare | | | | | |
|---|---|---|---|---|---|---|
| | 2000 | 1000 | 500 | 250 | 125 | 60 |
| rice "Yamabiko" | 5 | 6 | 7 | 8 | 9 | 9 |
| echinochloa c.g. | 1 | 1 | 1 | 1 | 1 | 1 |
| scirpus | 1 | 1 | 1 | 1 | 1 | 2 |
| monochoria | 1 | 1 | 1 | 1 | 1 | 2 |
| sagittaria | 4 | 4 | 4 | 5 | 6 | 8 |

| Tested plant | Compound No. 1.05 in g a.i. per hectare | | | | | |
|---|---|---|---|---|---|---|
| | 2000 | 1000 | 500 | 250 | 125 | 60 |
| rice "Yamabiko" | 9 | 9 | 9 | 9 | 9 | 9 |
| echinochloa c.g. | 1 | 1 | 1 | 1 | 3 | 3 |
| scirpus | 1 | 1 | 1 | 1 | 1 | 3 |
| monochoria | 1 | 1 | 1 | 1 | 1 | 3 |
| sagittaria | 4 | 4 | 4 | 6 | 8 | 9 |

| Tested plant | Compound No. 1.08 in g a.i. per hectare | | | | | |
|---|---|---|---|---|---|---|
| | 2000 | 1000 | 500 | 250 | 125 | 60 |
| rice "Yamabiko" | 8 | 8 | 9 | 9 | 9 | 9 |
| echinochloa c.g. | 1 | 1 | 1 | 1 | 1 | 2 |
| scirpus | 1 | 1 | 1 | 1 | 1 | 1 |
| monochoria | 1 | 1 | 1 | 1 | 1 | 1 |

-continued

| Tested plant | Compound No. 1.08 in g a.i. per hectare | | | | | |
|---|---|---|---|---|---|---|
| | 2000 | 1000 | 500 | 250 | 125 | 60 |
| sagittaria | 6 | 6 | 8 | 9 | 9 | 9 |

| Tested plant | Compound No. 1.09 in g a.i. per hectare | | | | | |
|---|---|---|---|---|---|---|
| | 2000 | 1000 | 500 | 250 | 125 | 60 |
| rice "Yamabiko" | 7 | 8 | 9 | 9 | 9 | 9 |
| echinochloa c.g. | 1 | 1 | 1 | 1 | 1 | 1 |
| scirpus | 1 | 1 | 1 | 1 | 1 | 4 |
| monochoria | 1 | 1 | 1 | 2 | 2 | 5 |
| sagittaria | 5 | 7 | 7 | 9 | 9 | 9 |

| Tested plant | Compound No. 1.29 in g a.i. per hectare | | | | | |
|---|---|---|---|---|---|---|
| | 2000 | 1000 | 500 | 250 | 125 | 60 |
| rice "Yamabiko" | 8 | 9 | 9 | 9 | 9 | 9 |
| echinochloa c.g. | 1 | 1 | 1 | 1 | 2 | 4 |
| scirpus | 1 | 1 | 1 | 1 | 1 | 2 |
| monochoria | 1 | 1 | 1 | 1 | 1 | 3 |
| sagittaria | 7 | 8 | 8 | 9 | 9 | 9 |

| Tested plant | Compound No. 1.66 in g a.i. per hectare | | | | | |
|---|---|---|---|---|---|---|
| | 2000 | 1000 | 500 | 250 | 125 | 60 |
| rice "Yamabiko" | 3 | 6 | 7 | 8 | 8 | 9 |
| echinochloa c.g. | 1 | 1 | 1 | 1 | 1 | 1 |
| scirpus | 1 | 1 | 1 | 1 | 1 | 2 |
| monochoria | 1 | 1 | 1 | 1 | 1 | 1 |
| sagittaria | 3 | 4 | 4 | 4 | 5 | 6 |

| Tested plant | Compound No. 1.73 in g a.i. per hectare | | | | | |
|---|---|---|---|---|---|---|
| | 2000 | 1000 | 500 | 250 | 125 | 60 |
| rice "Yamabiko" | 6 | 7 | 8 | 9 | 9 | 9 |
| echinochloa c.g. | 1 | 1 | 1 | 1 | 1 | 2 |
| scirpus | 1 | 1 | 1 | 1 | 1 | 2 |
| monochoria | 1 | 1 | 1 | 1 | 1 | 1 |
| sagittaria | 3 | 4 | 4 | 5 | 7 | 9 |

We claim:

1. A chemical compound having the formula

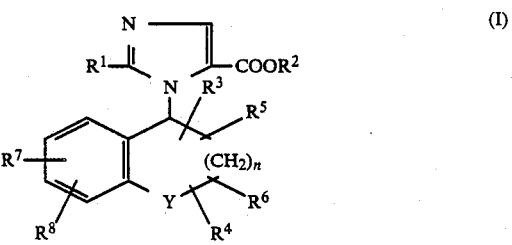

or a stereochemically isomeric form thereof, or a salt thereof, or a quaternised form thereof, or a N-oxide thereof, wherein $R^1$ is hydrogen or mercapto, $R^2$ is hydrogen, $C_1$-$C_7$alkyl, $C_3$-$C_7$alkenyl, $C_3$-$C_7$alkynyl, $C_3$-$C_7$cycloalkyl, $C_1$-$C_7$alkyloxy-$C_1$-$C_7$alkyl or aryl$C_1$-$C_5$alkyl;

n is zero, one or two;

Y is a group $-CH_2-S(O)_m-$, $-CH_2-O-$, $-CH_2-N(E)-$, or $-CH=N-$, wherein the hereoatom is linked to the carbon atom of the benzene ring and wherein m is zero, one or two;

E is hydrogen, $C_1$-$C_5$alkyl, $C_1$-$C_5$alkanoyl, or 4-methylphenylsulfonyl;

$R^3$, $R^4$, $R^5$ and $R^6$ are each independently hydrogen, $C_1$-$C_6$alkyl, mono- and di-(aryl)$C_1$-$C_5$alkyl, $C_1$-$C_6$alkyloxy, halo, $C_3$-$C_7$alkenyl, $C_1$-$C_5$alkyl substituted with one to three halo atoms, $C_1$-$C_5$alkyloxy substituted with one to three halo atoms or aryl; or $R^3$ and $R^4$ together may form a fused benzene residue which may be substituted with one or two substituents each independently selected from hydrogen, $C_1$-$C_5$alkyl, $C_1$-$C_5$alkyloxy, halo, $C_1$-$C_5$alkyl substituted with one to three halo atoms, $C_1$-$C_5$alkyloxy substituted with one to three halo atoms, nitro, amino and $-NH-CO-G$; or where $R^3$ and $R^4$ are geminally substituted, they may form a spirocyclic carbon ring with 3 to 7 carbon atoms; and $R^7$ and $R^8$ are each independently hydrogen, $C_1$-$C_5$alkyl, $C_1$-$C_5$alkyloxy, halo, $C_1$-$C_5$alkyl substituted with one to three halo atoms, $C_1$-$C_5$alkyloxy substituted with one to three halo atoms, cyano, nitro, amino, mono- and di-$C_1$-$C_5$alkylamino or $-NH-CO-G$;

G is $C_1$-$C_6$alkyl; and aryl is phenyl or phenyl substituted with one to three substituents each independently selected from $C_1$-$C_5$alkyll, $C_1$-$C_5$alkyloxy and halo;

whereby the radicals $R^3$, $R^4$, $R^5$ and $R^6$ as defined above may be substituted to any carbon atom making up the Y containing part of the bicyclic ring system, including the $CH_2$ or CH-groups of either the $-(CH_2)_n-$ or $-CH_2S-$, $-CH_2O-$, $-CH_2N(E)-$ or $-CH=N-$ fragments.

2. A compound according to claim 1, wherein $R^2$ is hydrogen or $C_1$-$C_7$alkyl; Y is $-CH_2-O-$, $-CH_2-N(E)-$ or $-CH_2-S-$; $R^3$, $R^4$, $R^5$ and $R^6$ are each independently hydrogen, $C_1$-$C_6$alkyl, aryl or (aryl)-$C_1$-$C_5$alkyl, or where $R^3$ and $R^4$ are geminally substituted they may form a spirocyclic carbon ring with 3 to 7 carbon atoms; and $R^7$ and $R^8$ are each independently hydrogen, $C_1$-$C_5$alkyl, $C_1$-$C_5$alkyloxy, halo or cyano.

3. A compound according to claim 2, wherein $R^2$ is hydrogen or $C_1$-$C_4$alkyl; n is zero or one; $R^3$ and $R^4$ are each independently hydrogen or $C_1$-$C_4$alkyl, or where $R^3$ and $R^4$ are geminally substituted they may form a spirocyclic carbon ring with 3 to 7 carbon atoms; $R^5$ and $R^6$ are both hydrogen; and $R^7$ and $R^8$ are each independently hydrogen, methyl, methoxy or halo.

4. A compound according to claim 3, wherein $R^2$ is hydrogen or methyl; Y is $-CH_2-O-$; $R^3$ and $R^4$ are each independently hydrogen or $C_1$-$C_4$alkyl, or where $R^3$ and $R^4$ are geminally substituted they may form a cyclopentane or cyclohexane ring; and $R^7$ and $R^8$ are each independently hydrogen or halo.

5. A chemical compound according to claim 1, wherein the compound is selected from the group consisting of methyl 1-(2,3-dihydro-4H-1-benzopyran-4-yl)-1H-imidazole-5-carboxylate, methyl 1-(2,3-dihydro-2,2-dimethyl-4H-1-benzopyran-4-yl)-1H-imidazole-5-carboxylate, methyl 1-(6-bromo-2,3-di-hydro-4H-1-benzopyran-4-yl)-1H-imidazole-5-carboxylate, methyl 1-[3,4-dihydro-spiro[2H-1-benzopyran-2,1'-cyclohexan]-4-yl]-1H-imidazole-5-carboxylate, methyl 1-[3,4-dihydrospiro[2H-1-benzopyran-2,1'-cyclopentan]-4-yl]-1H-imidazole-5-carboxylate, methyl 1-[3,4-dihydrospiro[2H-1-benzopyran-2,1'-cyclopentan]-4-yl]-2-mercapto-1H-imidazole-5-carboxylate, methyl (trans)-1-(2,3-dihydro-2-methyl-4H-1-benzopyran-4-yl)-1H-imidazole-5-carboxylate, methyl 1-(2,3-dihydro-2,3-dimethyl-4H-1-benzopyran-4-yl)-1H-imidazole-5-carboxylate, and methyl 1-(2,3-dihydro-3,3-dimethyl-4H-1-benzopyran-4-yl)-1H-imidazole-5-carboxylate.

6. A method for controlling weeds, which method comprises applying to said weeds or to the locus thereof a herbicidally effective amount of a 1-heterocyclyl-1H-imidazole-5-carboxylic acid derivative of formula

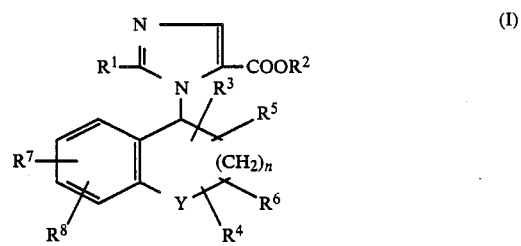

or a stereochemically isomeric form thereof, or a salt thereof, or a quaternised form thereof, or a N-oxide thereof, wherein $R^1$ is hydrogen or mercapto, $R^2$ is hydrogen, $C_1$-$C_7$alkyl, $C_3$-$C_7$alkenyl, $C_3$-$C_7$alkynyl, $C_3$-$C_7$cycloalkyl, $C_1$-$C_7$alkyloxy-$C_1$-$C_7$alkyl or aryl$C_1$-$C_5$alkyl;

n is zero, one or two;

Y is a group $-CH_2-S(O)_m-$, $-CH_2-O-$, $-CH_2-N(E)-$, or $-CH=N-$, wherein the hereoatom is linked to the carbon atom of the benzene ring and wherein m is zero, one or two;

E is hydrogen, $C_1$-$C_5$alkyl, $C_1$-$C_5$alkanoyl, or 4-methylphenylsulfonyl;

$R^3$, $R^4$, $R^5$ and $R^6$ are each independently hydrogen, $C_1$-$C_6$alkyl, mono- and di-(aryl)$C_1$-$C_5$alkyl, $C_1$-$C_6$alkyloxy, halo, $C_3$-$C_7$alkenyl, $C_1$-$C_5$alkyl substituted with one to three halo atoms, $C_1$-$C_5$alkyloxy substituted with one to three halo atoms or aryl; or $R^3$ and $R^4$ together may form a fused benzene residue which may be substituted with one or two substituents each independently selected from hydrogen, $C_1$-$C_5$alkyl, $C_1$-$C_5$alkyloxy, halo, $C_1$-$C_5$alkyl substituted with one to three halo atoms, $C_1$-$C_5$alkyloxy substituted with one to three halo atoms, nitro, amino and $-NH-CO-G$; or where $R^3$ and $R^4$ are geminally substituted, they may form a spirocyclic carbon ring with 3 to 7 carbon atoms; and $R^7$ and $R^8$ are each independently hydrogen, $C_1$-$C_5$alkyl, $C_1$-$C_5$alkyloxy, halo, $C_1$-$C_5$alkyl substituted with one to three halo atoms, $C_1$-$C_5$alkyloxy substituted with one to three halo atoms, cyano, nitro, amino, mono- and di-$C_1$-$C_5$alkylamino or $-NH-CO-G$;

G is $C_1$-$C_6$alkyl; and aryl is phenyl or phenyl substituted with one to three substituents each independently selected from $C_1$-$C_5$alkyl, $C_1$-$C_5$alkyloxy and halo;

whereby the radicals $R^3$, $R^4$, $R^5$ and $R^6$ as defined above may be substituted to any carbon atom making up the Y containing part of the bicyclic ring system, including the $CH_2$ or CH-groups of either the $-(CH_2)_n-$ or $-CH_2S-$, $-CH_2O-$, $-CH_2-N(E)-$ or $-CH=N-$ fragments.

7. A method according to claim 6 for selectively controlling weeds in crops of useful plants.

8. A method according to claim 7 wherein the crop is rice.

9. A method according to claim 7 wherein the crop is maize.

10. A method according to claim 7 wherein the crop is cereal.

11. A method according to claim 8 wherein the rice plants are transplanted rice plantlets.

12. A method according to claim 8 wherein 0.01 to 5.0 kg of active ingredient per hectare are applied to areas where rice crops are grown.

13. A method according to claim 12 wherein 0.05 to 1.0 kg of the active ingredient is applied per kectare after transplanting the rice plantlets.

14. A method according to claim 6, wherein $R^2$ is hydrogen or $C_1$-$C_7$alkyl; Y is $-CH_2-O-$, $-CH_2-N(E)-$ or $-CH_2-S-$; $R^3$, $R^4$, $R^5$ and $R^6$ are each independently hydrogen, $C_1$-$C_6$alkyl, aryl or (aryl)-$C_1$-$C_5$alkyl, or where $R^3$ and $R^4$ are geminally substituted they may form a spirocyclic carbon ring with 3 to 7 carbon atoms; and $R^7$ and $R^8$ are each independently hydrogen, $C_1$-$C_5$alkyl, $C_1$-$C_5$alkyloxy, halo or cyano.

15. A method according to claim 14, wherein $R^2$ is hydrogen or $C_1$-$C_4$alkyl; n is zero or one; $R^3$ and $R^4$ are each independently hydrogen or $C_1$-$C_4$alkyl, or where $R^3$ and $R^4$ are geminally substituted they may form a spirocyclic carbon ring with 3 to 7 carbon atoms; $R^5$ and $R^6$ are both hydrogen; and $R^7$ and $R^8$ are each independently hydrogen, methyl, methoxy or halo.

16. A method according to claim 15, wherein $R^2$ is hydrogen or methyl; Y is $-CH_2-O-$; $R^3$ and $R^4$ are each independently hydrogen or $C_1$-$C_4$alkyl, or where $R^3$ and $R^4$ are geminally substituted they may form a cyclopentane or cyclohexane ring; and $R^7$ and $R^8$ are each independently hydrogen or halo.

17. A method compound according to claim 6, wherein the compound is selected from the group consisting of methyl 1-(2,3-dihydro-4H-1-benzopyran-4-yl)-1H-imidazole-5-carboxylate, methyl 1-(2,3-dihydro-2,2-dimethyl-4H-1-benzopyran-4-yl)-1H-imidazole-5-carboxylate, methyl 1-(6-bromo-2,3-dihydro-4H-1-benzopyran-4-yl)-1H-imidazole-5-carboxylate, methyl 1-[3,4-dihydro-spiro[2H-1-benzopyran-2,1'-cyclohexan]-4-yl]-1H-imidazole-5-carboxylate, methyl 1-[3,4-dihydrospiro[2H-1-benzopyran-2,1'-cyclopentan]-4-yl]-1H-imidazole-5-carboxylate, methyl 1-[3,4-di-hydrospiro[2H-1-benzopyran-2,1'-cyclopentan]-4-yl]-2-mercapto-1H-imidazole-5-carboxylate, methyl (trans)-1-(2,3-dihydro-2-methyl-4H-1-benzopyran-4-yl)-1H-imidazole-5-carboxylate, methyl 1-(2,3-dihydro-2,3-dimethyl-4H-1-benzopyran-4-yl)-1H-imidazole-5carboxylate and methyl 1-(2,3-dihydro-3,3-dimethyl-4H-1-benzopyran-4-yl)-1H-imidazole-5-carboxylate.

18. A herbicidal composition, comprising one or more inert carriers and, if desired, other adjuvants, and as active ingredient a herbicidally effective amount of a chemical compound having the formula

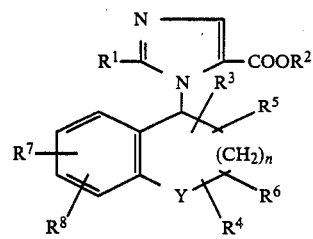

or a stereochemically isomeric form thereof, or a salt thereof, or a quaternised form thereof, or a N-oxide thereof, wherein $R^1$ is hydrogen or mercapto, $R^2$ is hydrogen, $C_1$-$C_7$alkyl, $C_3$-$C_7$alkenyl, $C_3$-$C_7$alkynyl, $C_3$-$C_7$cycloalkyl, $C_1$-$C_7$alkyloxy-$C_1$-$C_7$alkyl or aryl$C_1$-$C_5$alkyl;

n is zero, one or two;

Y is a group $-CH_2-S(O)_m-$, $-CH_2-O-$, $-CH_2-N(E)-$, or $-CH=N-$, wherein the hereoatom is linked to the carbon atom of the benzene ring and wherein m is zero, one or two;

E is hydrogen, $C_1$-$C_5$alkyl, $C_1$-$C_5$alkanoyl, or 4-methylphenylsulfonyl;

$R^3$, $R^4$, $R^5$ and $R^6$ are each independently hydrogen, $C_1$-$C_6$alkyl, mono- and di-(aryl)$C_1$-$C_5$alkyl, $C_1$-$C_6$alkyloxy, halo, $C_3$-$C_7$alkenyl, $C_1$-$C_5$alkyl substituted with one to three halo atoms, $C_1$-$C_5$alkyloxy substituted with one to three halo atoms or aryl; or $R^3$ and $R^4$ together may form a fused benzene residue which may be substituted with one or two substituents each independently selected from hydrogen, $C_1$-$C_5$alkyl, $C_1$-$C_5$alkyloxy, halo, $C_1$-$C_5$alkyl substituted with one to three halo atoms, $C_1$-$C_5$alkyloxy substituted with one to three halo atoms, nitro, amino and $-NH-CO-G$; or where $R^3$ and $R^4$ are geminally substituted, they may form a spirocyclic carbon ring with 3 to 7 carbon atoms; and $R^7$ and $R^8$ are each independently hydrogen, $C_1$-$C_5$alkyl, $C_1$-$C_5$alkyloxy, halo, $C_1$-$C_5$alkyl substituted with one to three halo atoms, $C_1$-$C_5$alkyloxy substituted with one to three halo atoms, cyano, nitro, amino, mono- and di-$C_1$-$C_5$alkylamino or $-NH-CO-G$;

G is $C_1$-$C_6$alkyl; and aryl is phenyl or phenyl substituted with one to three substituents each independently selected from $C_1$-$C_5$alkyl, $C_1$-$C_5$alkyloxy and halo;

whereby the radicals $R^3$, $R^4$, $R^5$ and $R^6$ as defined above may be substituted to any carbon atom making up the Y containing part of the bicyclic ring system, including the $CH_2$ or CH-groups of either the $-(CH_2)_n-$ or $-CH_2s-$, $-CH_2O-$, $-CH_2-N(E)-$ or $-CH=N-$ fragments.

19. A composition according to claim 18, wherein $R^2$ is hydrogen or $C_1$-$C_7$alkyl; Y is $-CH_2-O-$, $-CH_2-N(E)-$ or $-CH_2-S-$; $R^3$, $R^4$, $R^5$ and $R^6$ are each independently hydrogen, $C_1$-$C_6$alkyl, aryl or (aryl)-$C_1$-$C_5$alkyl, or where $R^3$ and $R^4$ are geminally substituted they may form a spirocyclic carbon ring with 3 to 7 carbon atoms; and $R^7$ and $R^8$ are each independently hydrogen, $C_1$-$C_5$alkyl, $C_1$-$C_5$alkyloxy, halo or cyano.

20. A composition according to claim 19, wherein $R^2$ is hydrogen or $C_1$-$C_4$alkyl; n is zero or one; $R^3$ and $R^4$ are each independently hydrogen or $C_1$-$C_4$alkyl, or where $R^3$ and $R^4$ are geminally substituted they may form a spirocyclic carbon ring with 3 to 7 carbon atoms; $R^5$ and $R^6$ are both hydrogen; and $R^7$ and $R^8$ are each independently hydrogen, methyl, methoxy or halo.

21. A composition according to claim 20, wherein $R^2$ is hydrogen or methyl; Y is —CH$_2$—O—; $R^3$ and $R^4$ are each independently hydrogen or C$_1$–C$_4$alkyl or where $R^3$ and $R^4$ are geminally substituted they may form a cycloentane or cyclohexane ring; and $R^7$ and $R^8$ are each independently hydrogen or halo.

22. A composition compound according to claim 18, wherein the compound is selected from the group consisting of methyl 1-(2,3-dihydro-4H-1-benzopyran-4-yl)-1H-imidazole-5-carboxylate, methyl 1-(2,3-dihydro-2,2-dimethyl-4H-1-benzopyran-4-yl)-1H-imidazole-5-carboxylate, methyl 1-(6-bromo-2,3-dihydro-4H-1-benzopyran-4-yl)-1H-imidazole-5-carboxylate, methyl 1-[3,4-dihydro-spiro[2H-1-benzopyran-2,1'-cyclohexan]-4-yl]-1H-imidazole-5-carboxylate, methyl 1-[3,4-dihydrospiro[2H-1-benzopyran-2,1'-cyclopentan]-4-yl]-1H-imidazole-5-carboxylate, methyl 1-[3,4-dihydrospiro[2H-1-benzopyran-2,1'-cyclopentan]-4-yl]-2-mercapto-1H-imidazole-5-carboxylate, methyl (trans)-1-(2,3-dihydro-2-methyl-4H-1-benzopyran-4-yl)-1H-imidazole-5-carboxylate, methyl 1-(2,3-dihydro-2,3-dimethyl-4H-1-benzopyran-4-yl)-1H-imidazole-5-carboxylate and methyl 1-(2,3-dihydro-3,3-dimethyl-4H-1-benzopyran-4-yl)-1H-imidazole-5-carboxylate.

* * * * *